US009993522B2

(12) United States Patent
Garcia-Caballero et al.

(10) Patent No.: US 9,993,522 B2
(45) Date of Patent: Jun. 12, 2018

(54) TREATMENT OF PAIN BY INHIBITION OF USP5 DE-UBIQUITINASE

(71) Applicant: UTI LIMITED PARTNERSHIP, Calgary (CA)

(72) Inventors: Agustin Garcia-Caballero, Calgary (CA); Vinicius Gadotti, Calgary (CA); Norbert Weiss, Calgary (CA); Gerald W. Zamponi, Calgary (CA)

(73) Assignee: UTI LIMITED PARTNERSHIP, Calgary (CA)

( * ) Notice: Subject to any disclaimer, the term of this patent is extended or adjusted under 35 U.S.C. 154(b) by 153 days.

(21) Appl. No.: 14/427,332

(22) PCT Filed: Sep. 17, 2013

(86) PCT No.: PCT/IB2013/002781
§ 371 (c)(1),
(2) Date: Mar. 11, 2015

(87) PCT Pub. No.: WO2014/045126
PCT Pub. Date: Mar. 27, 2014

(65) Prior Publication Data
US 2015/0231203 A1    Aug. 20, 2015

Related U.S. Application Data

(60) Provisional application No. 61/702,573, filed on Sep. 18, 2012.

(51) Int. Cl.
*A61K 38/16*    (2006.01)
*C07K 14/00*    (2006.01)
*C07K 14/47*    (2006.01)
*A61K 38/17*    (2006.01)
*C12N 15/113*   (2010.01)
*A61K 31/7088*  (2006.01)
*A61K 45/06*    (2006.01)

(52) U.S. Cl.
CPC ...... *A61K 38/1709* (2013.01); *A61K 31/7088* (2013.01); *A61K 45/06* (2013.01); *C07K 14/47* (2013.01); *C12N 15/1137* (2013.01); *C12N 2310/14* (2013.01)

(58) Field of Classification Search
None
See application file for complete search history.

(56) References Cited

FOREIGN PATENT DOCUMENTS

WO    WO 2010/081971    7/2010

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Extended European Search Report issued in European Application No. 13839267.5, dated Mar. 18, 2016.
Love et al., "Mechanisms, biology and inhibitors of deubiquitinating enzymes," *Nature Chemical Biology*, 3(11):697-705, 2007.
Bourinet and Zamponi, "Voltage gated calcium channels as targets for analgesics" *Curr. Top. Med. Chem.*, 5:539-546, 2005.
Bourinet et al., "Silencing of the Cav3.2 T-type calcium channel gene in sensory neurons demonstrates its major role in nociception" *Embo., J.* 24, 315-24, 2005.
Dayal et al., "Suppression of the deubiquitinating enzyme USP5 causes the accumulation of unanchored polyubiquitin and the activation of p53," *J. Biol. Chem.*, 284:5030-5041, 2008.
Duan et al., "PI3-kinase/Akt pathway-regulated membrane insertion of acid-sensing ion channel 1a underlies BDNF-induced pain hypersensitivity" *J. Neurosci.* 32:6351-63, 2012.
Issaenko et al., "Chalcone-based small-molecule inhibitors attenuate malignant phenotype via targeting deubiquitinating enzymes," *Cell Cycle*, 11(9):1804-1817, 2012.
Jacus et al., "Presynaptic Cav3.2 channels regulate excitatory neurotransmission in nociceptive dorsal horn neurons" *J. Neurosci.*, 32: 9374-82, 2012.
Jagodic et al., "Cell-specific alterations of T-type calcium current in painful diabetic neuropathy enhance excitability of sensory neurons" *J. Neurosci.*, 27: 3305-16, 2007.
Kapuria et al., "Protein cross-linking as a novel mechanism of action of a ubiquitin-activating enzyme inhibitor with anti-tumor activity," *Biochem. Pharm.*, 82:341-349, 2011.
Marangoudakis et al., "Differential ubiquitination and proteasome regulation of Ca(V)2.2 N-type channel splice isoforms," *J. Neurosci.*, 32(30):10365-10369, 2012.
Marger et al., "T-type calcium channels contribute to colonic hypersensitivity in a rat model of irritable bowel syndrome" *Proc. Natl. Acad. Sci. USA*, 108:11268-73, 2011.
Meregalli et al., "Bortezomib-induced painful neuropathy in rats: a behavioral, neurophysiological and pathological study in rats" *Eur. J. Pain*, 14:343-50, 2010.
Messinger et al., "In vivo silencing of the Ca(V)3.2 T-type calcium channels in sensory neurons alleviates hyperalgesia in rats with streptozocin-induced diabetic neuropathy" *Pain*, 145:184-95, 2009.
Munyendo et al., "Cell penetrating peptides in the delivery of biopharmaceuticals," *Biomolecules*, 2:187-202, 2012.
PCT International Search Report and Written Opinion issued in International Patent Application No. PCT/IB2013/002781, dated Sep. 17, 2013.
Simms et al., "Trafficking and stability of voltage-gated calcium channels," *Cell. Mol. Life Sci.*, 69:843-856, 2012.
Weiss et al., "A Ca(v)3.2/syntaxin-1A signaling complex controls T-type channel activity and low-threshold exocytosis" *J. Biol Chem.*, 287: 2810-8, 2012.

(Continued)

*Primary Examiner* — Christine J Saoud
*Assistant Examiner* — Jon M Lockard
(74) *Attorney, Agent, or Firm* — Parker Highlander PLLC

(57) ABSTRACT

The invention provides methods treating pain by inhibiting a Cav3.2 channel expression or function, including the use of contacting said channel in situ with an inhibitor of USP5 or an inhibitor of the interaction between Cav3.2 and USP5.

10 Claims, 13 Drawing Sheets

(56) References Cited

OTHER PUBLICATIONS

Wilkinson et al., "Metabolism of the polyubiquitin degradation signal: structure, mechanism, and role of isopeptidase T," *Biochemistry*, 34:14535-14546, 1995.

Yoshihara et al., "Insulin/insulin-like growth factor (IGF) stimulation abrogates an association between a deubiquitinating enzyme USP7 and insulin receptor substrates (IRSs) followed by proteasomal degradation of IRSs" *Biochem. Biophys. Res. Commun.* 423:122-7, 2012.

Zhang et al., "USP4 is regulated by AKT phosphorylation and directly deubiquitylates TGF-β type I receptor" *Nat. Cell. Biol.*, 14:717-26, 2012.

* cited by examiner

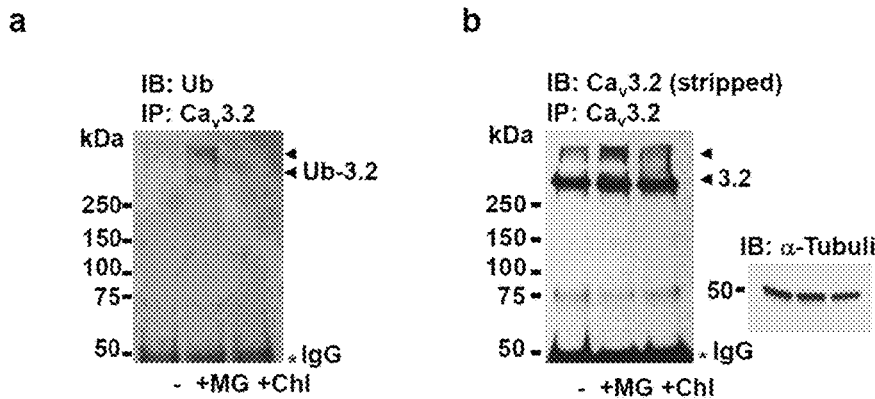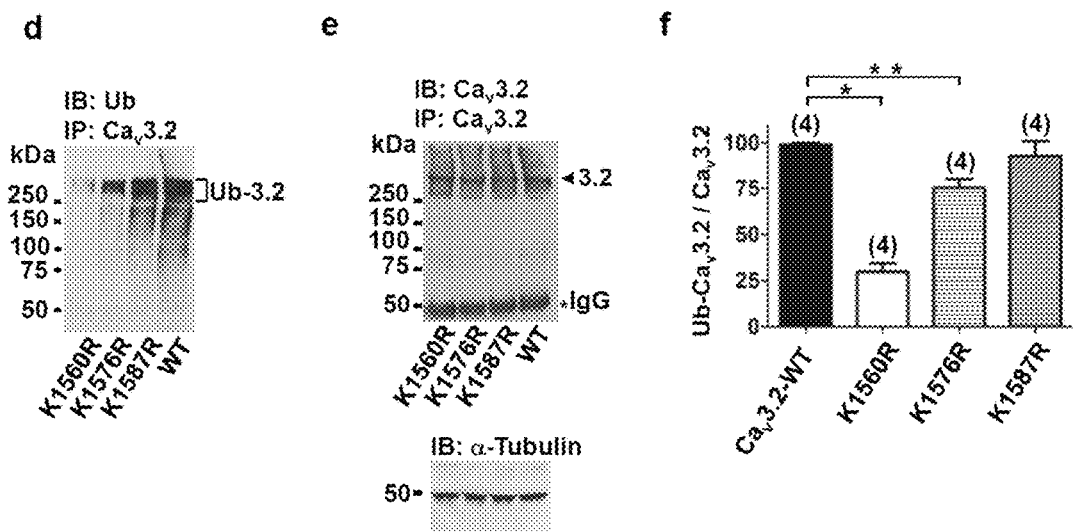
FIGS. 1A-F

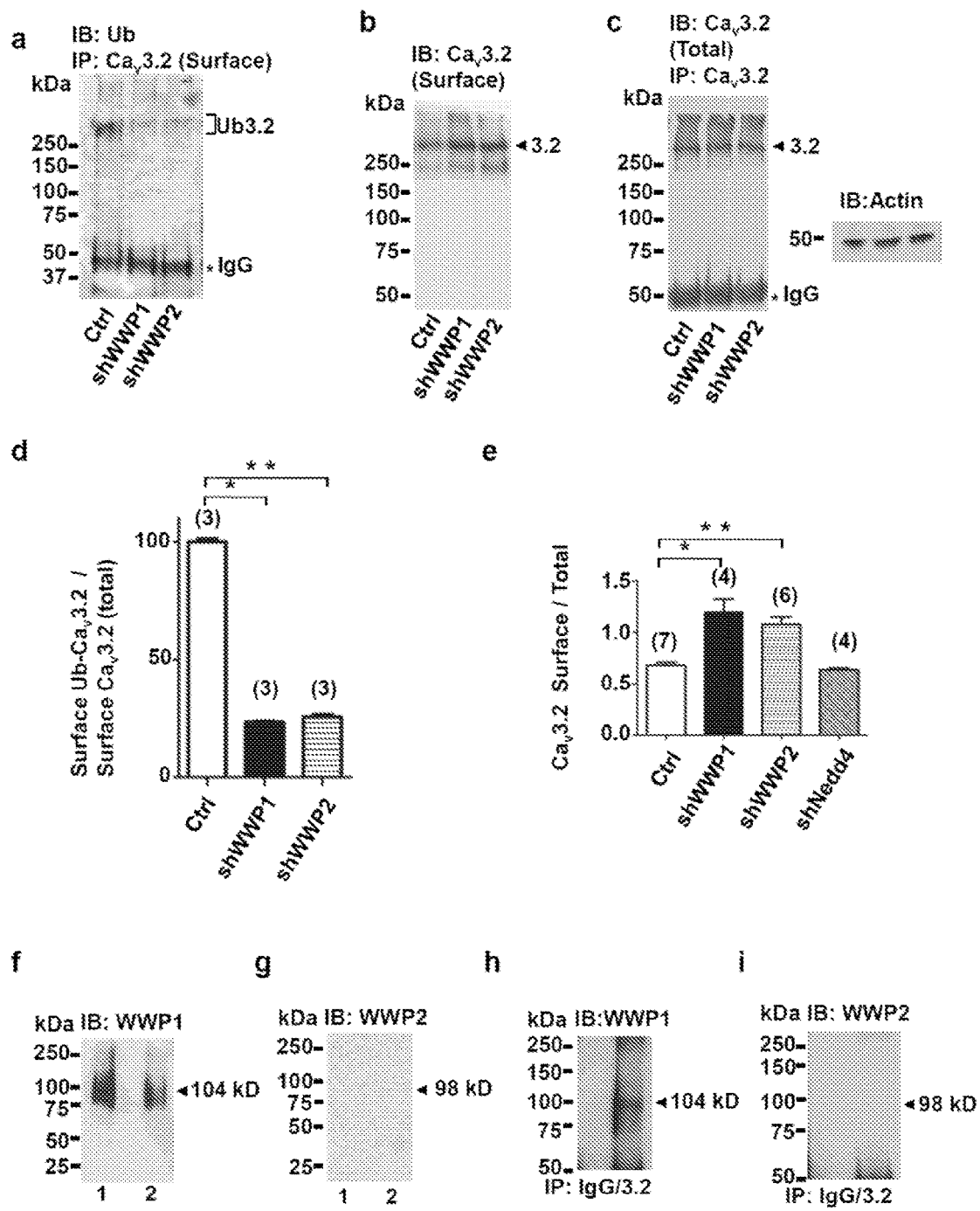
FIGS. 2A-I

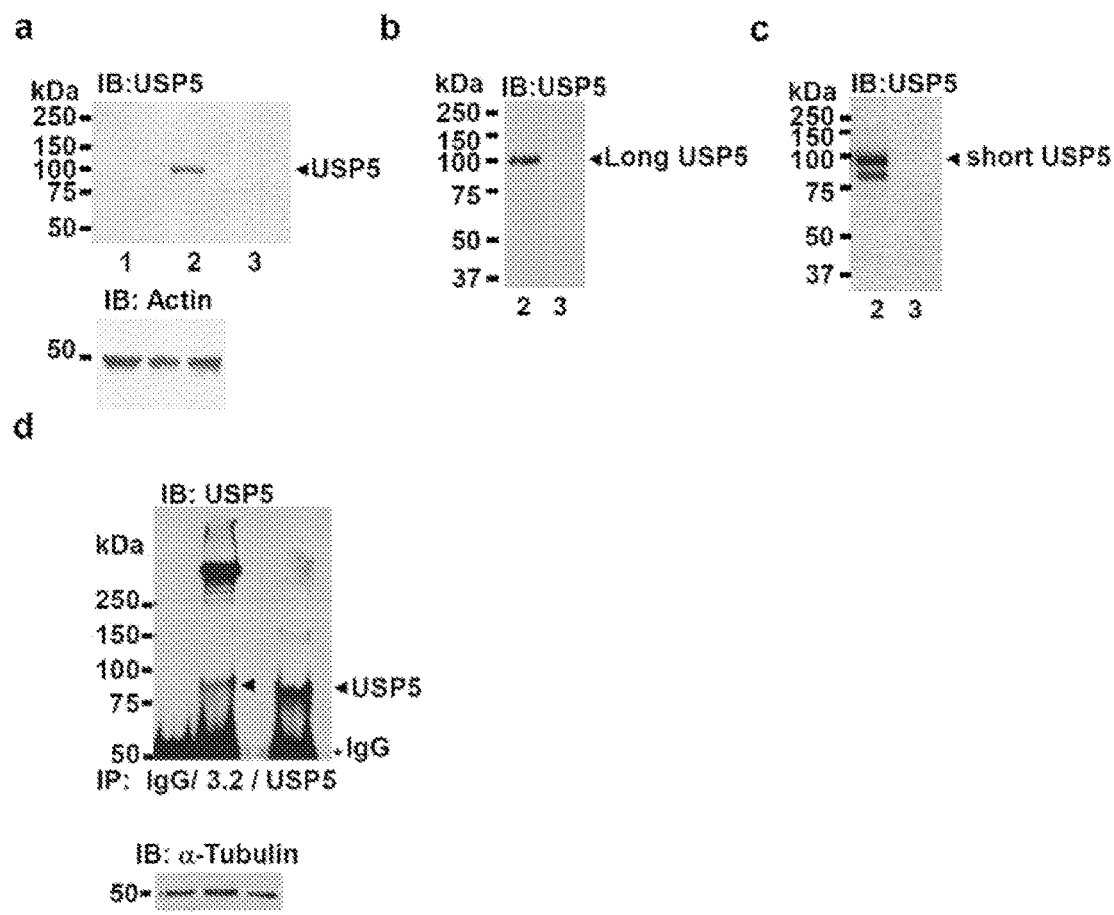
FIGS. 3A-D

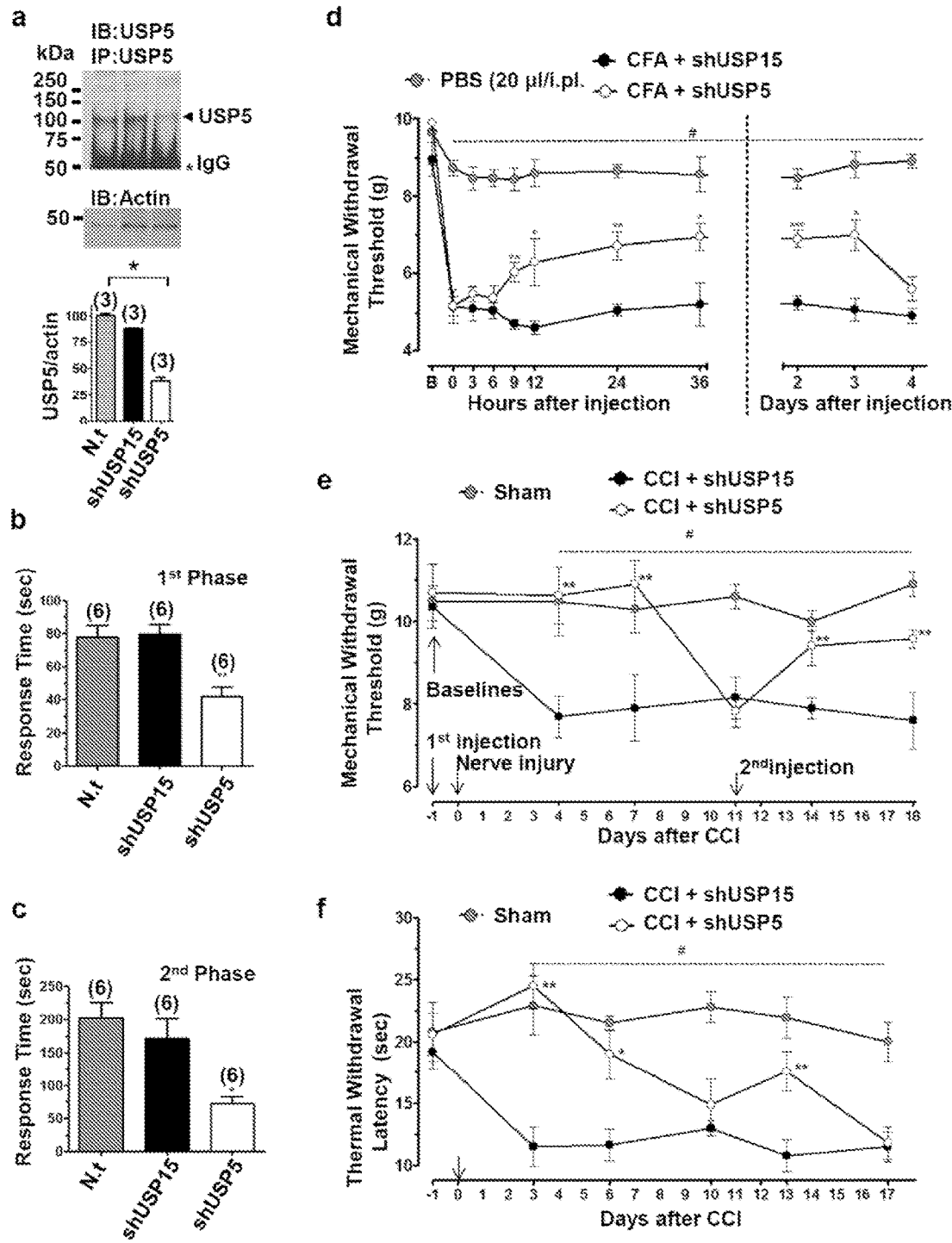
FIGS. 4A-F a
```
3.2-III-IV        -----------------EARRREEKRLRRLERRRRKAQ        1589    (SEQ ID NO: 1)
Tat-3.2-III-IV    YGRKKRRQRRREARRREEKRLRRLERRRRKAQ                       (SEQ ID NO: 2)
3.2-CT            -----------------MKHLEESNKEAREDAELDAEIELEM    1884    (SEQ ID NO: 54)
Tat-3.2-CT        YGRKKRRQRRRMKHLEESNKEAREDAELDAEIELEM                   (SEQ ID NO: 55)
Underline indicates alpha-helix prediction (http://bioinf.cs.ucl.ac.uk)
```
b 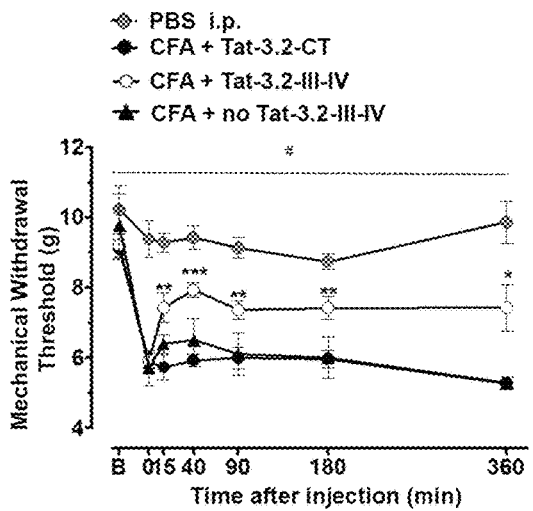
c 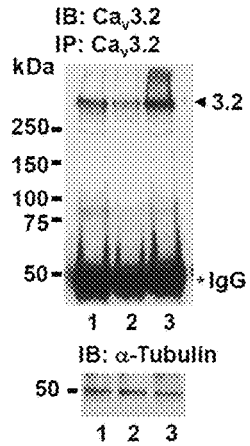
d 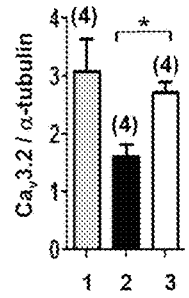
e 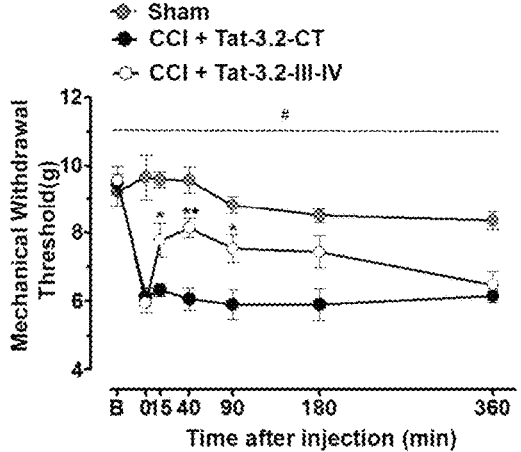
f 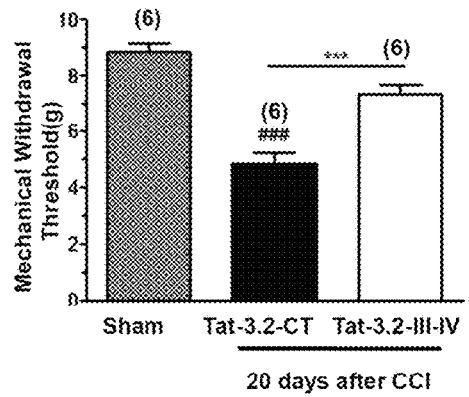
FIGS. 5A-F

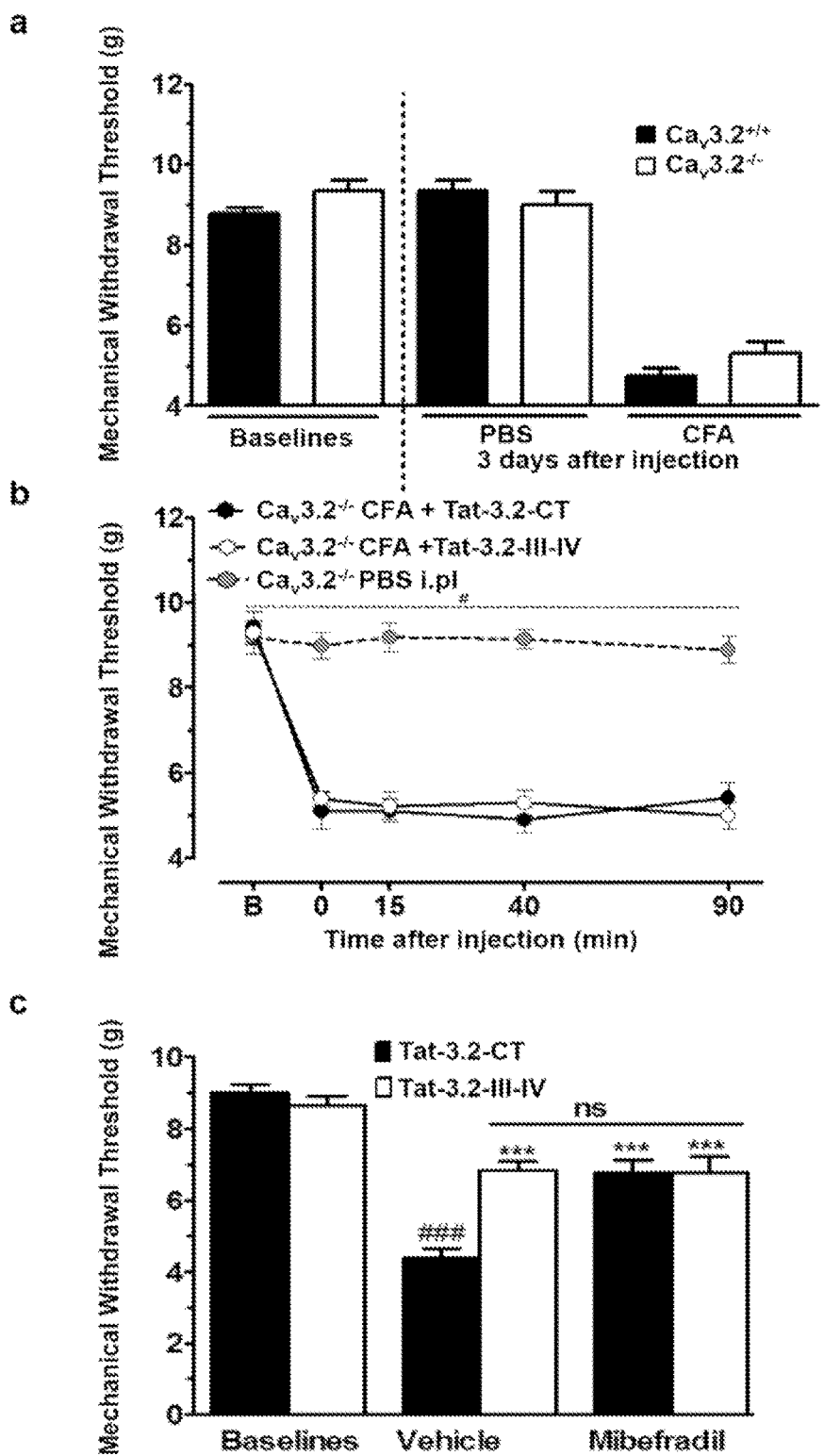
FIGS. 6A-C

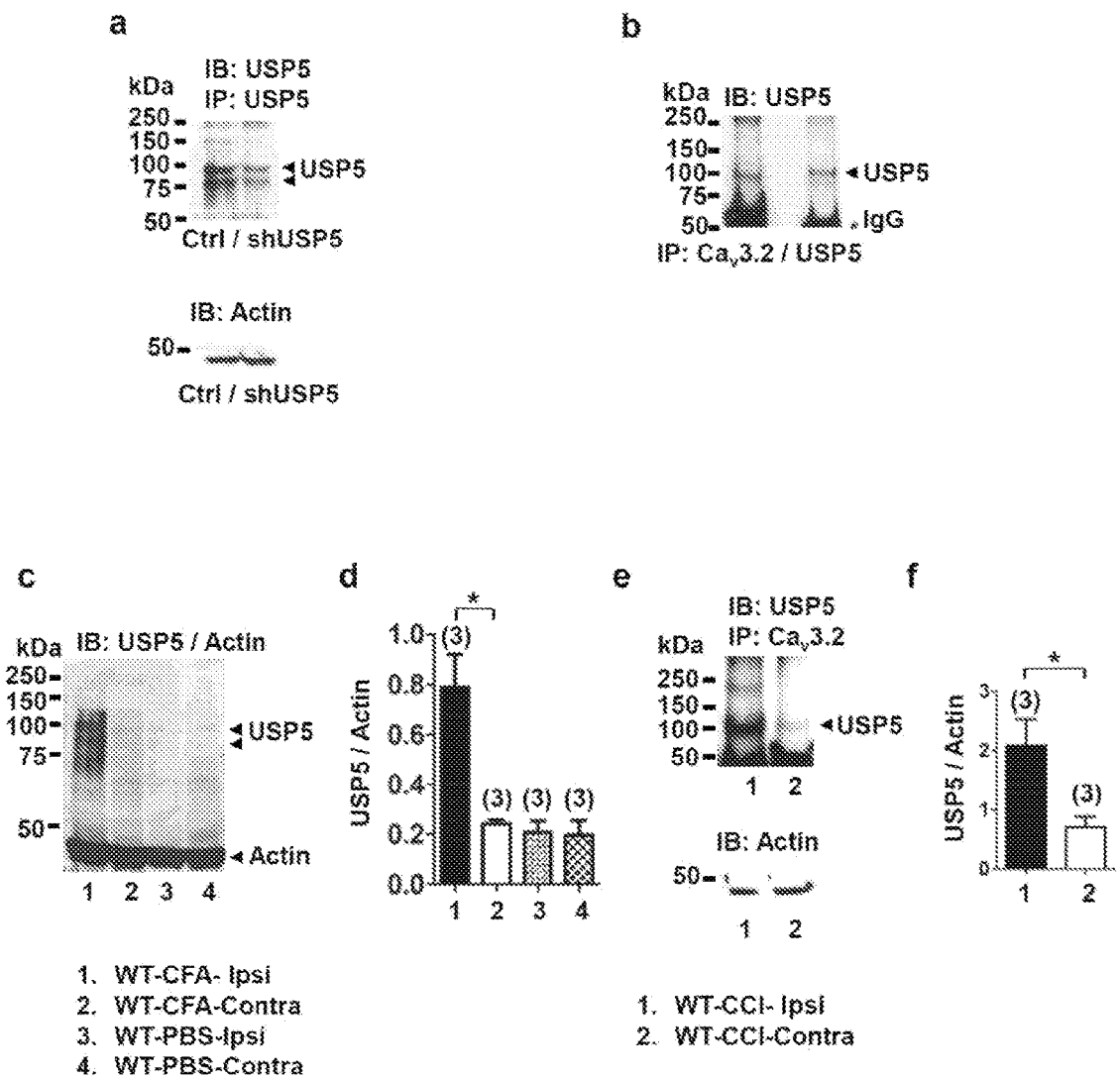
FIGS. 7A-F

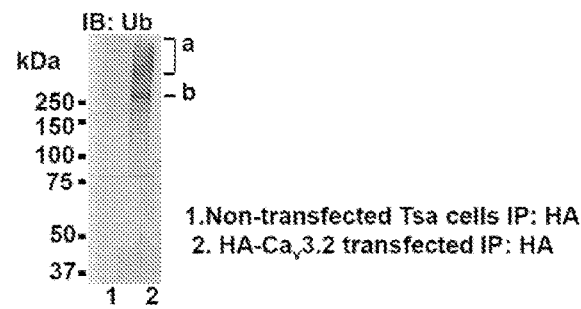
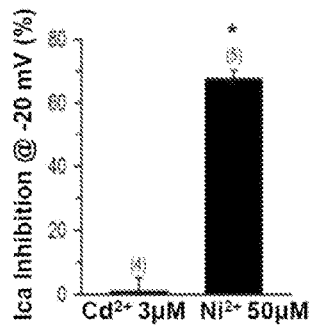
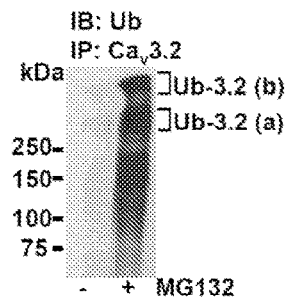
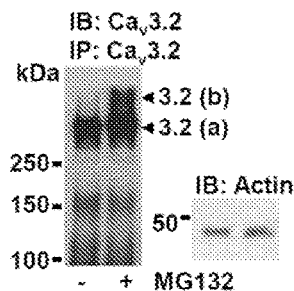
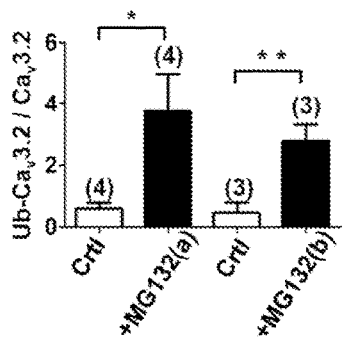
FIGS. 8A-F

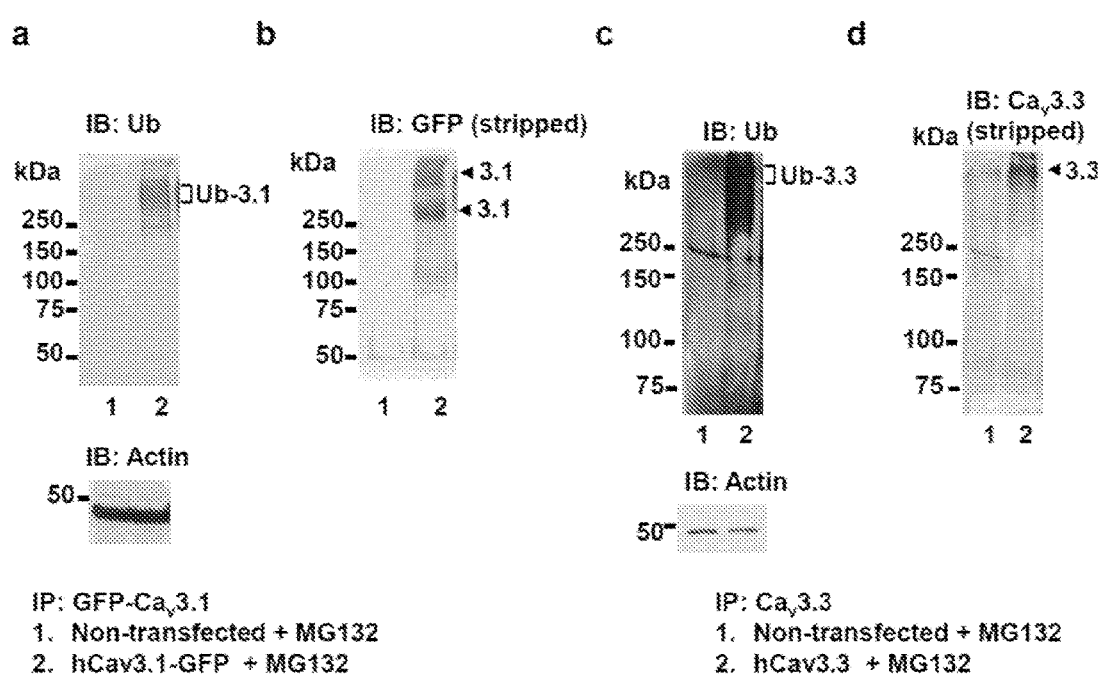
FIGS. 9A-D

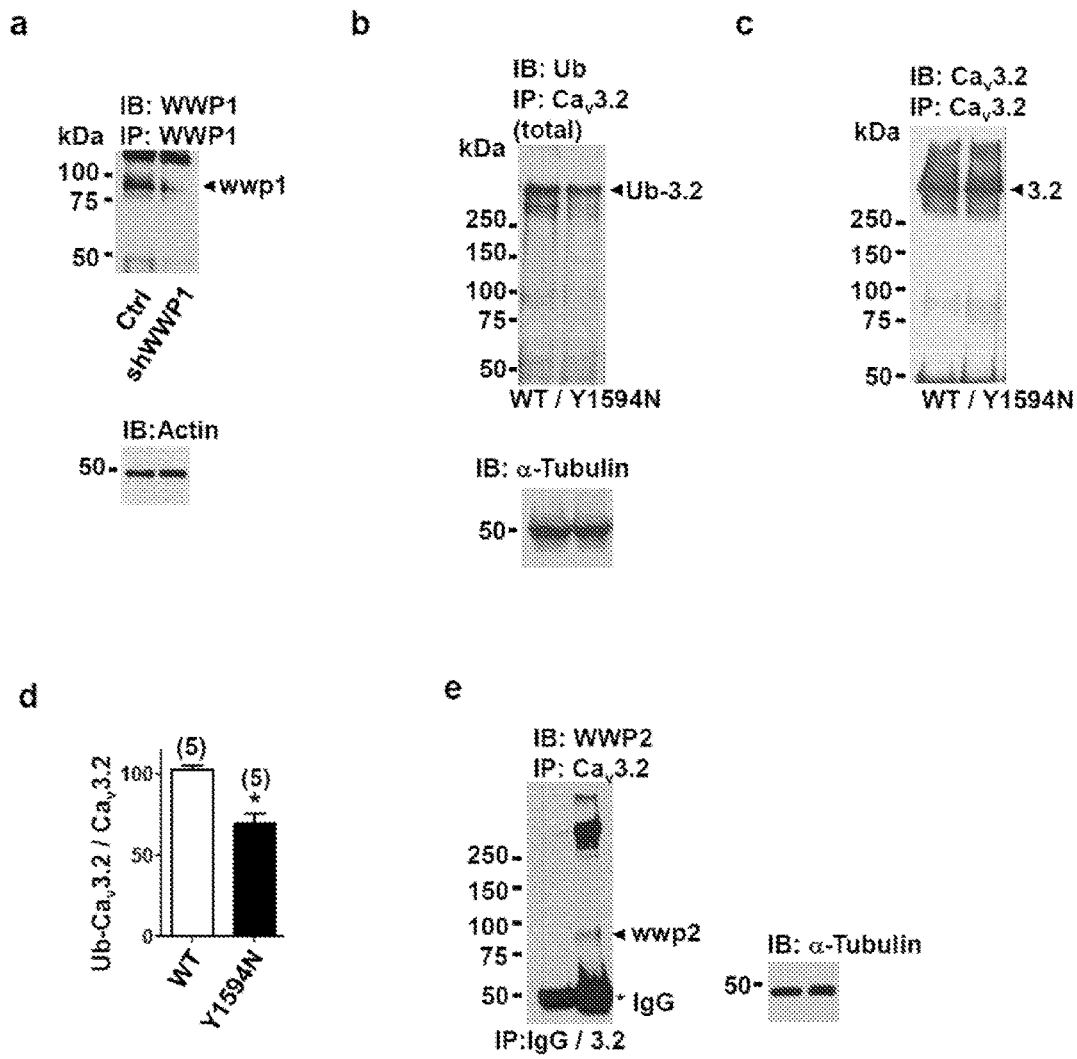
FIGS 10A-F

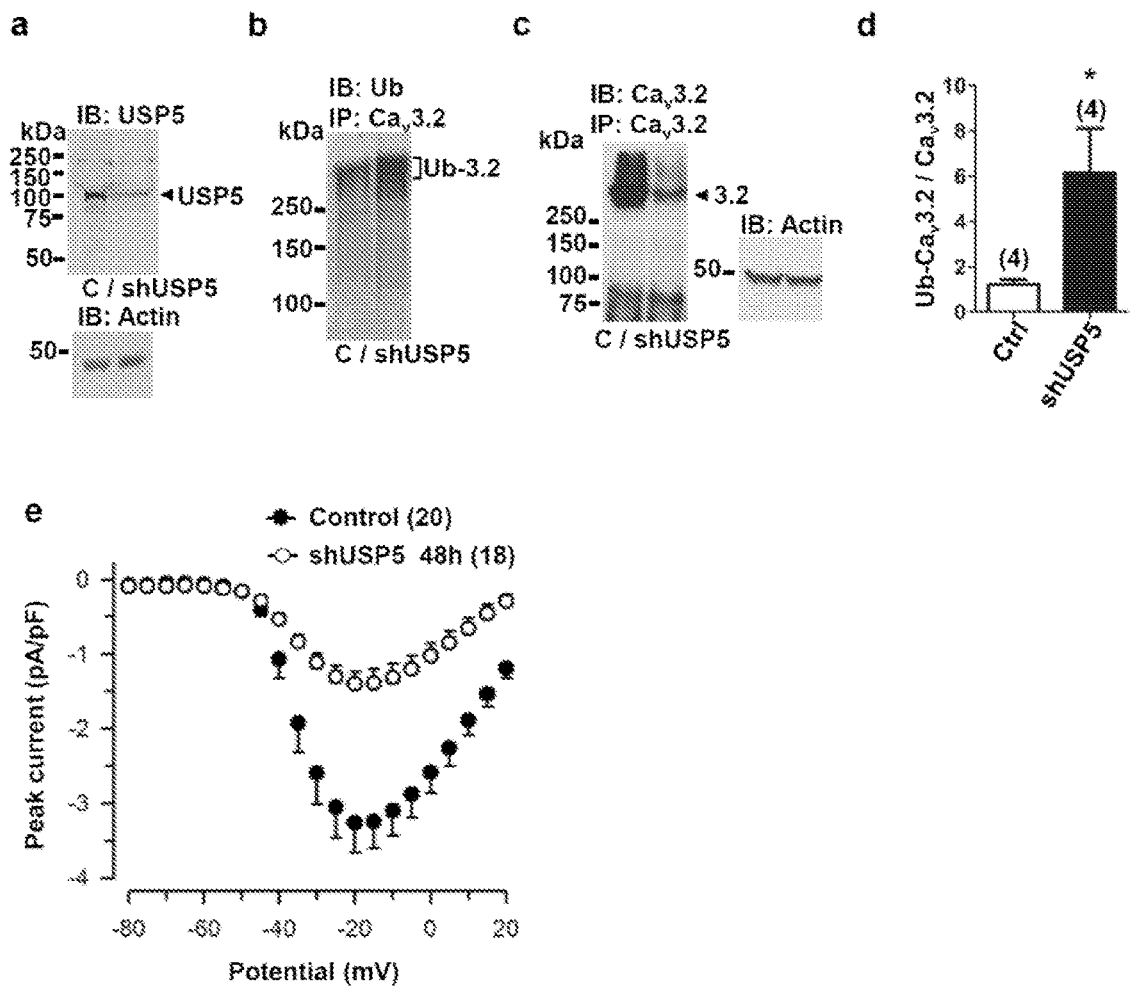
FIGS. 11A-E a
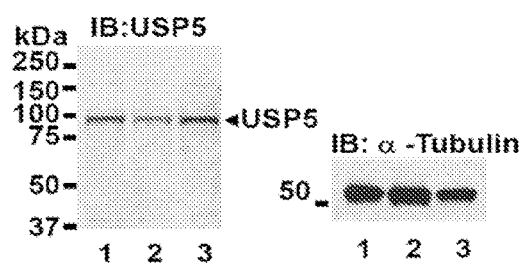
b
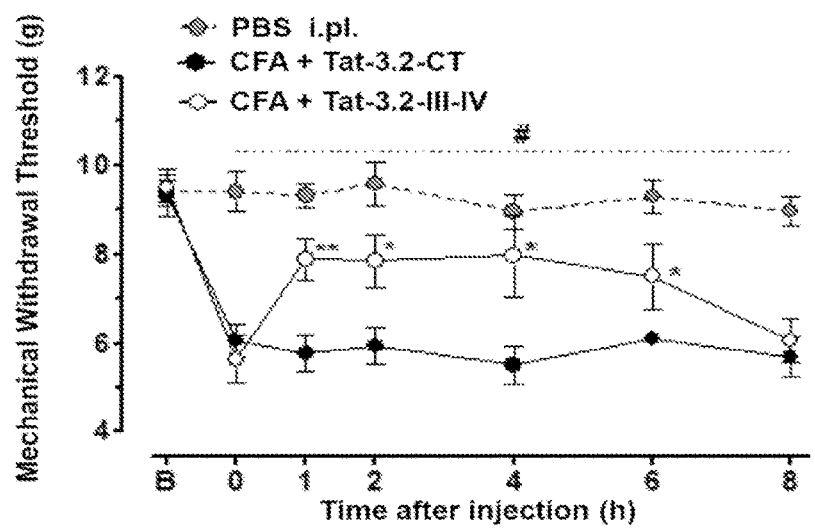
c
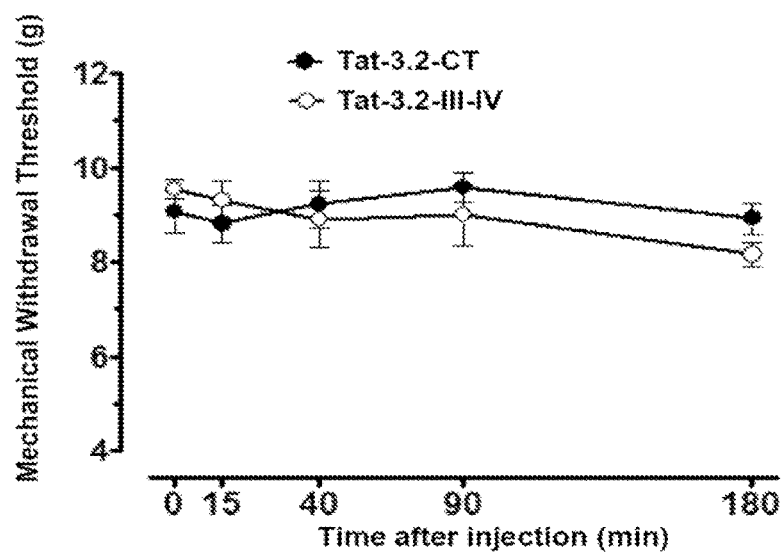
FIGS. 12A-C

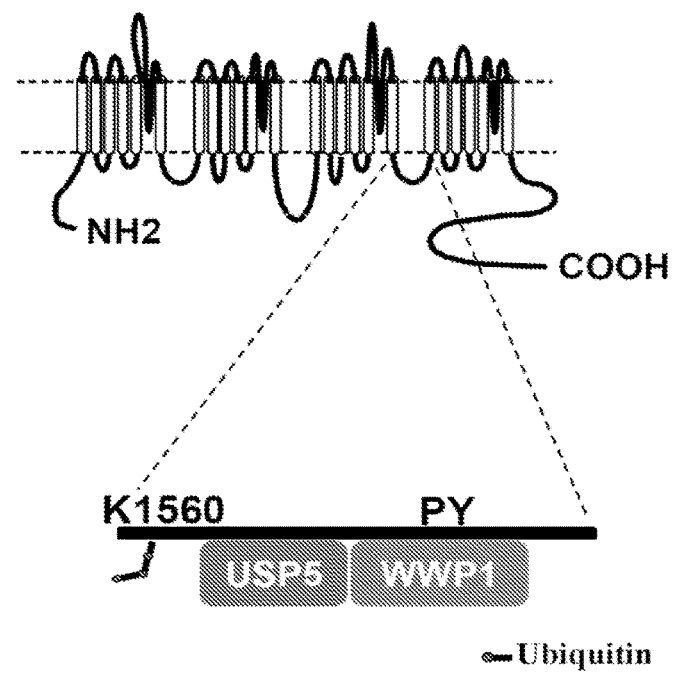
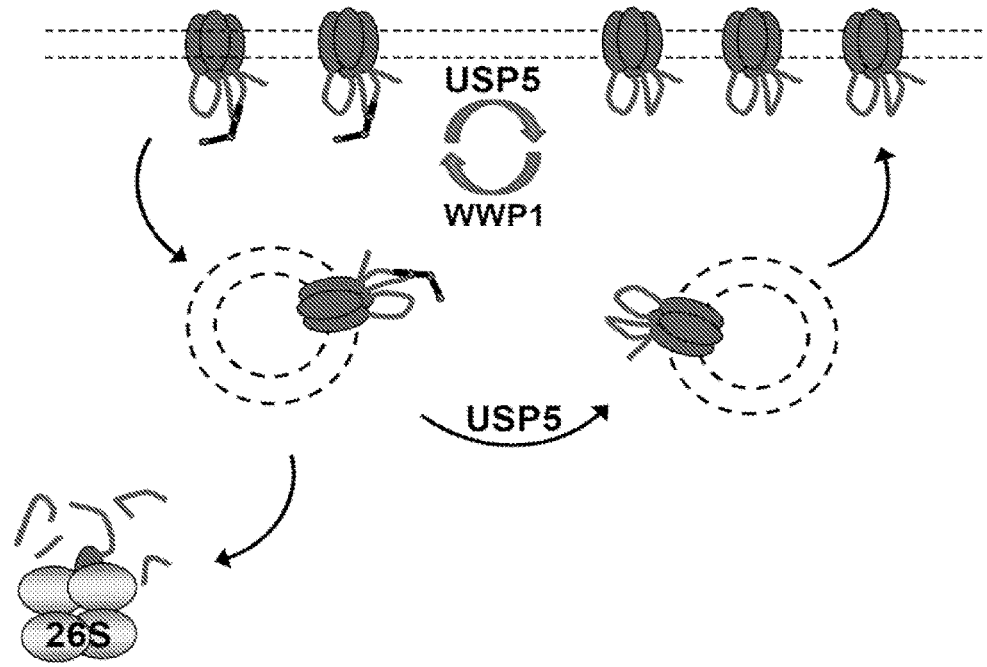
FIGS. 13A-B

TREATMENT OF PAIN BY INHIBITION OF USP5 DE-UBIQUITINASE

The present application is a national phase application under 35 U.S.C. § 371 of International Application No. PCT/IB2013/002781, filed Sep. 17, 2013, which claims benefit of priority to U.S. Provisional Application Ser. No. 61/702,573, filed Sep. 18, 2012. The entire contents of the above-referenced disclosures are specifically incorporated herein by reference.

The sequence listing that is contained in the file named "UNTIP0135US_ST25.txt", which is 14 KB (as measured in Microsoft Windows®) and was created on Mar. 10, 2015, is filed herewith by electronic submission and is incorporated by reference herein.

BACKGROUND OF THE INVENTION

1. Field of the Invention

This invention relates to the fields of medicine and cell biology. More specifically, it relates to the role of certain T-type calcium channels in pain signaling. In particular, it relates to inhibitors of USP5, and their use in controlling pain.

2. Related Art

Low-voltage activated (LVA) T-type calcium channels are essential contributors to signalling in electrically excitable cells. The vertebrate genome encodes three different types of T-type calcium channels (termed Cav3.1, Cav3.2 and Cav3.3, respectively) with specific expression patterns and unique functional and pharmacological profiles (Catterall and Few, 2008; Iftinca et al., 2009; Chen et al., 2003; Andreasen et al., 2000; Bourinet et al., 2005a; Bourinet et al., 2005b; Mangoni et al., 2006; McKay et al., 2006; Perez-Reyes et al., 2003). In addition, alternate splice isoforms of each of the Cav3 channel subtypes have been reported, and have been shown to give rise to channels with distinct functional properties (Catterall and Few, 2008; McKay et al., 2006; Molineux et al., 2006. At the molecular level, T-type channels are formed by a single pore that is comprised of four transmembrane domains that are connected by large cytoplasmic linkers. These linker regions form important protein interaction sites (Iftinca et al., 2011) and are the targets of second messenger systems such as protein kinases and G proteins (Iftinca et al., 2009).

In neurons, T-type channels regulate excitability and neuronal firing patterns, they activate calcium dependent signalling cascades, they contribute to low threshold exocytosis (Weiss et al., 2012), and they are pharmacological targets in neurological disorders such as epilepsy and pain. Indeed, the processing of pain signals via the afferent pain pathway is critically dependent on the activity of T-type calcium channels which not only shape the firing patterns of pain sensing neurons, but also contribute to the release of neurotransmitters at dorsal horn synapses (Jacus et al., 2012). Primary afferent pain fibers have their cell bodies in the dorsal root ganglia (DRG) and express predominantly the Cav3.2 T-type calcium channel subtype, with largest expression levels occurring in medium sized cells (Bourinet et al., 2005b). Genetic ablation of T-type channels, their knockdown via intrathecal delivery of antisense oligonucleotides, or their direct inhibition by small organic molecules results in an increased threshold of both mechanical and thermal pain thus validating T-type channels as a suitable pharmacological target (Bourinet et al., 2005a). T-type channel expression (and thus activity) in pain sensing neurons is upregulated in various pathological conditions linked to pain, including diabetic neuropathy, bowel inflammation, and nerve injury (Marger et al., 2011; Jagodic et al., 2007; Messinger et al., 2009), however, the molecular mechanisms by which this upregulation occurs are unknown. Nonetheless, it stands to reason that preventing this type of enhancement would be a suitable means of combating the development of pain, while sparing the normal function of these channels in other tissues such as the brain and the cardiovascular system.

One possible mechanism by which ion channel expression levels can be regulated is the ubiquitination and proteasomal degradation of these channels. Indeed, there is a large body of evidence in the literature that describes the ubiquitination of ion channels such as CFTR, ENaC and high voltage activated calcium channels by E3 ubiquitin ligases. Akin to the relationship between protein kinases and phosphatases, ubiquitin specific proteases (USP's) or deubiquitinases (DUB's) serve to remove ubiquitin groups from target proteins, leading to an increase in protein stability. However, their role in ion channel stability has been virtually unexplored.

SUMMARY OF THE INVENTION

Thus, in accordance with the present invention, there is provided a method of inhibiting a Cav3.2 channel comprising contacting said channel in situ with an inhibitor of USP5. The inhibitor may a protein, a nucleic acid or a small molecule. The may be a peptide or polypeptide competitor of USP5 binding to Cav3.2, such as a segment of Cav3.2 or USP, including a peptide fused to a cell penetrating peptide, such as a Tat domain, or a Cav3.2 linker III-IV peptide fused to a cell penetrating peptide domain such as a Tat domain. The inhibitor is an siRNA or an shRNA directed to USP5. The inhibitor may be a small molecule. The method may further comprise contacting said Cav3.2 channel with a second channel inhibitor, such as a second inhibitor of USP5.

In another embodiment, there is provided a method of treating pain in a subject comprising administering to said subject an inhibitor of USP5. The pain may be chronic pain, persistent pain, inflammatory pain or neuropathic pain. The inhibitor may be a protein, a nucleic acid or a small molecule. The inhibitor may be a peptide or polypeptide competitor of USP5 binding to Cav3.2, such as a segment of Cav3.2 or USP, including a peptide fused to a cell penetrating domain such as Tat domain, or a Cav3.2 linker III-IV peptide fused to a cell penetrating peptide domain such as a Tat domain. The inhibitor is an siRNA or an shRNA directed to USP5. The inhibitor may be a small molecule. The inhibitor is administered systemically, local to an area of pain, or regional to an area of pain. The inhibitor may be administered intravenously, intra-arterially, subcutaneously, topically, orally, intrathecally or opthalmicly. The inhibitor may be administered more than once, including chronically. The method may further comprise administering to said subject a second anti-pain agent, such as a second USP5 inhibitor, an anti-inflammatory agent (e.g., an NSAID, a steroidal agent or a tricyclic anti-depressant), or an opiate.

Also provided is a pharmaceutical composition comprising (a) a peptide of consisting of 10-75 residues, and (b) comprising a segment of Cav3.2 or USP5. The peptide may be fused to a cell penetrating peptide domain, such as a Tat domain, and may comprise a Cav3.2 linker III-IV peptide. The peptide may comprise the Cav3.2 sequence EAR-RREEKRLRRLERRRRKAQ (SEQ ID NO: 1), or the Cav3.2-Tat domain sequence YGRKKRRQRRREAR-RREEKRLRRLERRRRKAQ (SEQ ID NO: 2).

In yet another embodiment, there is provided a method of identifying an inhibitor of USP5 binding to Cav3.2 comprising (a) providing USP5 and Cav3.2 molecules comprising all or a fragment of each molecule, wherein said molecules retain the ability to bind to each other; (b) contacting said molecules with a candidate substance; and (c) determining the binding of said molecules in step (b), wherein a reduced binding of said molecules as compared to binding in the absence of said candidate substance indicates that said candidate substance is an inhibitor of USP5 binding to Cav3.2. The candidate substance may be a peptide, a peptidomimetic or a small molecule. One or both of said molecules are labeled, and said labels may provide quenching or energy transfer when binding occurs.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 1A-F. Neuronal Cav3.2 channels are ubiquitinated in the domain III-IV linker. (FIG. 1A) Western blot of ubiquitinated Cav3.2 channels immunoprecipitated via the H-300 antibody (Santa Cruz) from cultured mouse DRG neurons preincubated with 5 µM MG132 (MG) or 100 µM Chloroquine (Chl) overnight, as detected with an anti-ubiquitin antibody. (FIG. 1B) Cav3.2 immunoprecipitates from mouse DRG neurons probed with the H-300 antibody. The membrane from FIG. 1A was stripped and used for reprobing with the indicated antibody. The lower panel shows a loading control blot for α-tubulin using the same samples as in FIGS. 1A-B, but run on a separate gel. (FIG. 1C) Cav3.2 isoform 1 and isoform 2 III-IV linker sequence alignment. Arrows indicate lysines and underlined sequence indicates the PY motif (FIG. 1D) Ubiquitin signal of Cav3.2 WT and different lysine (K1560R, K1576R, K1587R) mutant channels from tsA-201 cell immunoprecipitates, a representative blot is shown, n=4. (FIG. 1E) Cav3.2 channel immunoprecipitates from tsA-201 cells of the total pool of channels are shown by western blot. The membrane from FIG. 1D was stripped and used for reprobing with an anti-Cav3.2 antibody. A blot for α-tubulin is shown as control (bottom panel). (FIG. 1F) Cav3.2 WT and mutant ubiquitinated signals were quantified by densitometry, normalized as a ratio of ubiquitinated-Cav3.2 versus Cav3.2 and expressed as percentage of the control (WT signal). Mean±SEM of WT Cav3.2: 99.00±0.9, n=4; Cav3.2 K1560R: 29.7±4.8, n=4, P<0.0001; Cav3.2 K1576R: 75.2±4.7, n=4, P<0.0024; Cav3.2 K1587R: 92.8±8.1 n=4, P<0.47.

FIGS. 2A-I. HECT E3 ligases WWP1 and WWP2 regulate Cav3.2 channels by ubiquitination. (FIG. 2A) Western blot of ubiquitinated surface Cav3.2 channels expressed in tsA-201 cells transfected with WWP1 or WWP2 shRNAs and pretreated with 5 µM MG132 overnight. After biotin labeling of cells, labeled surface proteins were enriched with neutravidin beads. Samples were eluted off the beads with RIPA buffer containing 4M guanidine at pH1.6, and samples were tumbled for 30 minutes at 4° C., before the samples were dialyzed overnight. Surface Cav3.2 channels were enriched by immunoprecipitation with an anti-Cav3.2 antibody and probed for ubiquitin. (FIG. 2B) Western blot of surface pool of Cav3.2 channels expressed in tsA-201 cells treated with WWP1 or WWP2 shRNAs. (FIG. 2C) Western blot of total pool of Cav3.2 channels expressed in tsA-201 cells treated with WWP1 or WWP2 shRNAs. An actin blot is shown as sample loading control for FIGS. 2A-C. (FIG. 2D) Quantification of ubiquitinated surface Cav3.2 channels by densitometry, normalized as a ratio of surface ubiquitinated-Cav3.2 versus surface Cav3.2 (Total Cav3.2) and expressed as percentage of the control, relative integrated density values from western blots. Data from 3 experiments are included in the bar chart (*P<0.05, t-test). Mean±SEM of control: 100±1.6, n=3; shWWP1: 23.4±0.3, n=3, P<0.0001; shWWP2: 25.6±0.99, n=3, P<0.0001. (FIG. 2E) Quantification of surface Cav3.2 channels expressed as the ratio of surface vs total channels by densitometry, relative integrated density values from western blots. Data from 4-7 experiments are included in the bar chart (*P<0.05, t-test). Mean±SEM of control: 0.68±0.03, n=7; shWWP1: 1.20±0.1, n=4, P=0.0006; shWWP2: 1.08±0.07, n=6, P=0.0002; shNedd4: 0.64±0.02, n=3, P=0.3571. (FIGS. 2F-G) Affinity purification assays were done using the following biotinylated peptides; human Cav3.2$_{1556-1602}$ (long III-IV linker, lane 1) Cav3.2$_{1569-1586}$ (short III-IV linker, lane 2) peptides. Mouse DRG lysates (500 µg) were incubated with each peptide (50 µg) and neutravidin beads for 2 hr at 4° C. Western blot analysis was performed using rabbit anti-WWP1 (FIG. 2F) and anti-WWP2 (FIG. 2G) antibodies. A representative immunoblot is shown (n=3). Western blot of Cav3.2 immunoprecipitates from mouse DRG lysates probed with an anti-WWP1 (FIG. 2H) or an anti-WWP2 antibodies (FIG. 2I).

FIGS. 3A-D. USP5 interactions with the Cav3.2 III-IV linker. (FIG. 3A) Affinity purification assays were done using the following biotinylated peptides; scrambled hCav3.2$_{1556-1602}$ (scramble, lane 1), human Cav3.2$_{1556-1602}$ (III-IV linker, lane 2), or Cav3.2$_{1860-1884}$ (CT, lane 3) peptides. Western blot analysis was performed using a rabbit antibody to USP5. A blot for actin is shown as loading control (bottom panel). A representative immunoblot is shown (n=3). In vitro binding assay of purified recombinant USP5 (long isoform (FIG. 3B) and short isoform (FIG. 3C)) to human Cav3.2$_{1556-1602}$ (III-IV linker, lane 2) or Cav3.2$_{1860-1884}$ (CT, lane 3) peptides. The asterisk indicates a degradation product of the USP5 short isoform. (FIG. 3D) USP5-Cav3.2 co-immunoprecipitation assay using mouse DRG tissue was performed by probing Cav3.2 immunoprecipitates for USP5 by western blot. A blot for α-tubulin is shown as loading control (bottom panel). A representative experiment is shown, n=3. This high MW (~350 KDa) band in the co-IP lane likely reflects an Igg aggregate that occasionally appears in co-IPs.

FIGS. 4A-F. Nociceptive response of mice treated with USP5-shRNA. (FIG. 4A) In vivo knockdown of USP5 via intrathecal delivery of shRNA against USP15 (as a control) and USP5. $L_5$ DRG were isolated and lysed, and USP5 immunoprecipitates were probed with an USP5 antibody. This experiment was repeated three times. The bar graph represents a quantification of the USP5 band intensity relative to the actin control for three different experiments. (FIGS. 4B-C) Blind analysis of the nocifensive behavior of mice not-treated (N.t) or treated i.t. with USP5-shRNA or USP15-shRNA (control) in the first (FIG. 4B) and second (FIG. 4C) phases of formalin-induced nociception. Each column represents the mean±SEM (n=5-6) and is representative of 2 independent experimental runs. A one-way ANOVA revealed a significant effect of USP5-shRNA treatment [$F_{(1,163)}$=4.4, p=0.0021) for the first, and [$F_{(14,08)}$=4.4, p=0.0135] for the second phase. (FIG. 4D) Time course of mechanical hyperalgesia of mice treated with USP5-shRNA or USP15-shRNA (12.5 μg/i.t.) under CFA-induced chronic inflammatory pain. Each circle represents the mean±S.E.M. (n=6-8), and is representative of 2 independent experiments. Two-way ANOVA revealed that paw withdrawal thresholds of mice receiving USP5-shRNA were significantly greater than those treated with USP15-shRNA (negative control). (FIGS. 4E-F) Time course of mechanical (FIG. 4E) and thermal (FIG. 4F) hyperalgesia of mice treated with USP5-shRNA or USP15-shRNA (12.5 μg/i.t.) under CCI-induced neuropathic pain. Each circle represents the mean±S.E.M. (n=5-6) and is representative of 2 independent sets of experiments. Two-way ANOVA revealed that spinal treatment of mice with USP5-shRNA significantly attenuated the mechanical hyperalgesia induced by CCI when compared with the CCI+USP15-shRNA (control) group. *P<0.05, P<0.01, *P<0.001.

FIGS. 5A-F. Antihyperalgesic effect of a Tat-Cav3.2-III-IV linker peptide in mouse models of chronic pain. (FIG. 5A) Sequence alignment of peptides used for in vivo mouse studies. (FIG. 5B) Blind analyses of the time course of mechanical hyperalgesia of mice treated with Tat-peptides or control peptides (10.0 μg/i.t.) under CFA-induced pain. 10.0 μg of peptide correspond to 2.27, 2.22 and 3.5 nmoles for the Tat-3.2-III-IV, Tat-3.2-CT and 3.2-III-IV peptides. (FIG. 5C) Cav3.2 immunoprecipitates from ipsilateral lumbar 5 ($L_5$) DRGs from naïve mice (lane1), or from CFA-injected mice treated with either Tat-3.2-III-IV linker (lane2) or Tat-3.2-CT (lane3) peptides, analyzed by western blot 90 minutes after i.t. treatment. A blot for α-tubulin is shown as loading control (bottom panel) (FIG. 5D) Quantification of Cav3.2 protein levels expressed as the ratio of Cav3.2 vs α-tubulin by densitometry. (FIG. 5E) Time course of mechanical hyperalgesia of mice treated with either the Tat-3.2-III-IV linker or the Tat-3.2-CT peptides (10.0 μg/i.t.) under CCI-induced neuropathy. (FIG. 5F) Effect of the Tat-3.2-CT and Tat-3.2-III-IV peptides when intrathecally delivered three weeks after CCI. The hatched symbols denote statistical significance relative to Sham (p<0.001). The experimenter was blind to the treatment. In all panels, each circle/bar represents the mean±S.E.M. (n=5-8) and is representative of 2 independent sets of experiments. Statistical analyses were performed by two-way ANOVA followed by Tukey's test. *P<0.05, P<0.01, *P<0.001.

FIGS. 6A-C. Effect of a Tat-Cav3.2-III-IV linker peptide on pain behavior of Cav3.2 null mice. (FIG. 6A) Baselines and mechanical hyperalgesia of wild type or Cav3.2 null mice following CFA injection. Each column represents the mean±S.E.M. (n=5-6) and are representative of 2 independent experiments. *P<0.05, **P<0.01. (FIG. 6B) Blind analyses of the time course of mechanical hyperalgesia of Cav3.2 null mice treated with the Tat-3.2-III-IV linker or the Tat-3.2-CT peptides (10.0 μg/i.t.) under CFA-induced pain. Each circle represents the mean±S.E.M. (n=5-8) and data are representative of 2 independent sets of experiments. (FIG. 6C) Effects of Tat-3.2-III-IV (10.0 μg/i.t.) on mechanical withdrawal threshold in CFA injected mice treated with mibefradil (10.0 μg/i.t.). Note the lack of Tat-3.2-III-IV effect in mibefradil treated mice. Each circle represents the mean±S.E.M. (n=9-13) and data are representative of 2 independent sets of experiments. The experimenter was blinded to the experimental conditions. Statistical analyses were performed by three-way ANOVA followed by Tukey's test. *P<0.05, P<0.01, *P<0.001.

FIGS. 7A-F. USP5 regulation of Cav3.2 in dorsal horn. (FIG. 7A) In vivo knockdown of USP5 in dorsal horn tissue via intrathecal delivery of shRNA against USP5. (FIG. 7B) USP5-Cav3.2 co-immunoprecipitation from mouse dorsal horn tissue tissue. (FIG. 7C) Western blot analysis of USP5 expression $L_4$-$L_6$ dorsal horn tissue in naïve and CFA treated mice and (FIG. 7D) quantification relative to actin control. Note the upregulation of USP5 on the ipsilateral side in CFA treated mice. (FIG. 7E) Co-immunoprecipiation of Cav3.2 and USP from $L_4$-$L_6$ dorsal horn tissue in response to chronic constriction injury and (FIG. 7F) quantification relative to actin band intensity.

FIGS. 8A-F. Ubiquitination of neuronal Cav3.2 channels in tsA201 and CAD cells. (FIG. 8A) Immunoprecipitation of HA-Cav3.2 from tsA-201 cells, followed by probing with a ubiquitin antibody revealing a ubiquitin band just above 250 kDa and a high MW smear. Two bands (labeled a and b) were excised from the corresponding Coomassie gel and subjected to mass spectrometry analysis. (FIG. 8B) Mass spectrometry results from bands a and b from the Coomassie gel. (FIG. 8C) Calcium current sensitivity to 50 μM Nickel or 3 μM Cadmium from CAD cells showing the low voltage activated channels expressed in these cells are consistent with Cav3.2. (FIG. 8D) Western blot of ubiquitinated Cav3.2 channels from CAD neuronal cells preincubated with 5 μM MG132 overnight, as detected with an anti-ubiquitin antibody. (FIG. 8E) Cav3.2 immunoprecipitates probed with an antibody that recognizes amino acids 2174-2353 of human, rat and mouse Cav3.2 are shown. The membrane from FIG. 8D was stripped and probed as indicated. The lower panel shows a loading control blot for actin. Note the two bands for Cav3.2 and ubiquitin (labeled a and b) that may correspond to mono and poly-ubiquitinated channels. (FIG. 8F) Quantification of the effect of the proteasomal inhibitor MG132 (5 μM) on the ubiquitination state of Cav3.2 channels expressed as a ratio of ubiquitinated vs non-ubiquitinated channels (Ub-Cav3.2 channels/Cav3.2 channels), and obtained via relative integrated density values from western blots for both the lower (labeled a) and higher (labeled b) MW bands observed in FIG. 8D and FIG. 8E. Data from 3-4 experiments are included in the bar chart (*P<0.05, t-test). Mean±SEM of control (a): 0.54±0.26, n=5; 5 μM MG132: 3.2±1.1, n=5; Mean±SEM of control (b): 0.46±0.3, n=4; 5 μM MG132: 2.80±0.5, n=4.

FIGS. 9A-D. Ubiquitination of Cav3.1 and Cav3.3 channels. (FIGS. 9A-B) Western blot of an immunoprecipitate of a GFP-tagged human Cav3.1 channels transiently expressed in tsA-201 cells. The blot was probed with either a ubiquitin antibody (FIG. 9A) or with a GFP antibody after stripping (FIG. 9B). (FIGS. 9C-D) Same as in FIGS. 9A-B, but with human, non-tagged Cav3.3 channels. In all cases, MG132 was present.

FIGS. 10A-F. Ubiquitination of mutant Cav3.2 Y1594N channels. (FIG. 10A) WWP1 immunoprecipitates analyzed by Western blot with a specific anti-WWP1 antibody from tsa-201 cells transfected with WWP1-shRNA or vector alone (control). This experiment was repeated three times. (FIG. 10B) Western blot of ubiquitinated WT Cav3.2 and mutant Y1594N channels expressed in tsA-201 cells. An α-tubulin blot is shown as sample loading control. (FIG. 10C) Western blot of WT Cav3.2 and mutant Y1594N channel immunoprecipitates from tsA-201 cells. Membrane from FIG. 10B, was stripped and used to reprobe with anti-Cav3.2 antibody. (FIG. 10D) Quantification of ubiquitinated Cav3.2 channels expressed as the ratio of ubiquitinated-Cav3.2 vs total Cav3.2 channels by densitometry (measured via from relative integrated density values from western blots). Data from 5 experiments are included in the bar chart (*P<0.05, t-test). Mean±SEM of control: 103.0±2.1, n=5; Cav3.2 Y1594N: 69.4±6.4, n=5, P=0.0010. (FIG. 10E) IgG immunoprecipitates as control (lane 1) or Cav3.2 immunoprecipitates (lane 2) from mouse brain lysate probed with anti-WWP2 antibody. Total whole lysates (input) were probed for alpha-tubulin (right panel). (FIG. 10F) Interacting proteins from mouse brain lysates that bind to the hCav3.2$_{1556-1602}$-III-IV linker peptide as identified by mass-spectrometry.

FIGS. 11A-E. USP5 regulates Cav3.2 ubiquitin modification and channel activity. (FIG. 11A) USP5 western blot of whole cells lysates from CAD cells transfected with or without USP5-shRNA. A representative experiment is shown, n=3. (FIG. 11B) Cav3.2 immunoprecipitates probed for ubiquitin by western blot from CAD cells pretreated with 5 μM MG132 and transfected with USP5-shRNA or USP15-shRNA (control), as detected with an anti-ubiquitin antibody. A representative experiment is shown, n=4. (FIG. 11C) Cav3.2 immunoprecipitates probed for Cav3.2 are shown from a stripped membrane used in panel b. A blot for actin is shown as loading control (right panel). A representative experiment is shown, n=4. (FIG. 11D) Quantification of the USP5-shRNA effect on the ubiquitination state of Cav3.2 channels expressed as a ratio of ubiquitinated vs. non-ubiquitinated channels (Ub-Cav3.2 channels/Cav3.2 channels), obtained from relative integrated density values from western blots. Data from 4 experiments are included in the bar chart (*P<0.05, t-test). Mean±SEM of control: 1.22±0.2, n=4; shUSP5: 6.13±2.0, n=4. (FIG. 11E) Cav3.2 channel peak currents of CAD cells transfected with shRNA for USP5 or eGFP.

FIGS. 12A-C. In vivo effect of a Tat-Cav3.2-III-IV linker peptide. (FIG. 12A) In vitro competition assay by affinity precipitation using biotinylated or non-biotinylated peptides and mouse brain lysates, analyzed by western blot using an anti-USP5 antibody. Lane 1, a biotin-Tat-3.2 III-IV$_{1569-1589}$ linker alone (25 μg) or lane 2, a biotin-Tat-3.2-III-IV$_{1569-1589}$ linker (25 μg)+Tat-3.2-III-IV$_{1569-1589}$ linker (50 μg) or lane 3, a biotin-Tat-3.2 III-IV$_{1569-1589}$ linker (25 μg)+Tat-3.2-CT$_{1860-1884}$ linker (50 μg). A loading control blot for α-tubulin is shown in right panel. (FIG. 12B) Time course of mechanical hyperalgesia of mice treated intraperitoneally (i.p.) with the Tat-3.2-III-IV linker peptide (15 mg/kg) under CFA-induced pain. Each column represents the mean±SEM (n=6-8) and is representative of 2 independent experimental runs. Statistical analyses were performed by two-way ANOVA followed by Tukey's test. ***P<0.001. (FIG. 12C) Time course of basal mechanical threshold of non-injured mice treated with the Tat-3.2-III-IV linker or control peptide (10.0 μg/i.t). Statistical analyses were performed by two-way ANOVA followed by Tukey's test. Each column represents the mean±SEM (n=5) and is representative of 2 independent experimental runs. N.s.=non-significant.

FIGS. 13A-B Regulation of Cav3.2 channels by ubiquitination and deubiquitination. (FIG. 13A) Schematic representation of the membrane topology of the Cav3.2 channel. The domain III-IV linker appears to be a hot spot for channel regulation by ubiquitination. It contains key ubiquitination sites (i.e., residue 1560) as well as binding sites for the ubiquitin ligase WWP1 (PY motif) and USP5. (FIG. 13B) Cav3.2 channels are ubiquitinated by WWP1 and de-ubiquitinated by USP5. Ubiquitinated channels are less stable in the plasma membrane, and are thus internalized and subject to degradation. Enhanced association of the channel with USP5 results in an increased population of deubiquitinated (and thus more stable) channels. It is possible that deubiqutination may also occur on endosomes, leading to recycling of channels.

DESCRIPTION OF ILLUSTRATIVE EMBODIMENTS

Here, the inventors report for the first time the regulation of T-type channels by a ubiquitin specific protease, USP5, that binds to and regulates low voltage gated calcium channel activity. They also show that the ubiquitination state of Cav3.2 channels is regulated by an interplay of the E3 ligase WWPI and USP5 that occurs at the intracellular domain III-IV linker and which fine tunes the stability of T-type channel protein in the plasma membrane. Finally, they demonstrate that disrupting USP5 regulation in vivo either via knockdown or by the use of competing Tat peptides increases ubiquitination and decreases Cav3.2 channel activity, leading to analgesia in models of inflammatory and neuropathic pain. These data thus identify a previously unappreciated avenue for the analgesia.

I. USP5

Ubiquitin carboxyl-terminal hydrolase 5 is an enzyme that in humans is encoded by the USP5 gene. It binds one zinc ion as a cofactor.

USP5 cleaves linear and branched multiubiquitin polymers with a marked preference for branched polymers. It is involved in unanchored 'Lys-48'-linked polyubiquitin disassembly, and binds linear and 'Lys-63'-linked polyubiquitin with a lower affinity. Knock-down of USP5 causes the accumulation of p53/TP53 and an increase in p53/TP53 transcriptional activity because the unanchored polyubiquitin that accumulates is able to compete with ubiquitinated p53/TP53 but not with MDM2 for proteasomal recognition. It catalyzes thiol-dependent hydrolysis of ester, thioester, amide, peptide and isopeptide bonds formed by the C-terminal Gly of ubiquitin (a 76-residue protein attached to proteins as an intracellular targeting signal).

USP5 has been shown to interact with TADA3L and TRIML1. The UBP-type zinc finger domain interacts selectively with an unmodified C-terminus of the proximal ubiquitin. Both UBA domains are involved in polyubiquitin recognition.

II. PAIN

Pain is an unpleasant feeling often caused by intense or damaging stimuli. The International Association for the Study of Pain's widely used definition states: "Pain is an unpleasant sensory and emotional experience associated with actual or potential tissue damage, or described in terms of such damage."

Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation in the United States. It is a major symptom in many medical conditions, and can significantly interfere with a person's quality of life and general functioning. Psychological factors such as social support, hypnotic suggestion, excitement, or distraction can significantly modulate pain's intensity or unpleasantness.

The International Association for the Study of Pain (IASP) has classified pain according to specific characteristics: (1) region of the body involved (e.g., abdomen, lower limbs), (2) system whose dysfunction may be causing the pain (e.g., nervous, gastrointestinal), (3) duration and pattern of occurrence, (4) intensity and time since onset, and (5) etiology. This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system (neuropathic pain, see hereunder) or by its abnormal function (dysfunctional pain, like in fibromyalgia, irritable bowel syndrome, tension type headache, etc.).

Duration.

Pain is usually transitory, lasting only until the noxious stimulus is removed or the underlying damage or pathology has healed, but some painful conditions, such as rheumatoid arthritis, peripheral neuropathy, cancer and idiopathic pain, may persist for years. Pain that lasts a long time is called chronic, and pain that resolves quickly is called acute. Traditionally, the distinction between acute and chronic pain has relied upon an arbitrary interval of time from onset; the two most commonly used markers being 3 months and 6 months since the onset of pain, though some theorists and researchers have placed the transition from acute to chronic pain at 12 months. Others apply acute to pain that lasts less than 30 days, chronic to pain of more than six months duration, and subacute to pain that lasts from one to six months. A popular alternative definition of chronic pain, involving no arbitrarily fixed durations is "pain that extends beyond the expected period of healing." Chronic pain may be classified as cancer pain or benign.

Nociceptive.

Nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). As subst of nocicipetive pain is called "inflammatory" pain, as it results from tissue damage and the response of innate inflammatory responses. Nociceptive pain may also be divided into "visceral," "deep somatic" and "superficial somatic" pain. Visceral structures are highly sensitive to stretch, ischemia and inflammation, but relatively insensitive to other stimuli that normally evoke pain in other structures, such as burning and cutting. Visceral pain is diffuse, difficult to locate and often referred to a distant, usually superficial, structure. It may be accompanied by nausea and vomiting and may be described as sickening, deep, squeezing, and dull. Deep somatic pain is initiated by stimulation of nociceptors in ligaments, tendons, bones, blood vessels, fasciae and muscles, and is dull, aching, poorly localized pain. Examples include sprains and broken bones. Superficial pain is initiated by activation of nociceptors in the skin or other superficial tissue, and is sharp, well-defined and clearly located. Examples of injuries that produce superficial somatic pain include minor wounds and minor (first degree) burns.

Neuropathic.

Neuropathic pain is caused by damage or disease affecting any part of the nervous system involved in bodily feelings (the somatosensory system). Peripheral neuropathic pain is often described as "burning," "tingling," "electrical," "stabbing," or "pins and needles." Bumping the "funny bone" elicits acute peripheral neuropathic pain.

Phantom.

Phantom pain is pain felt in a part of the body that has been lost or from which the brain no longer receives signals. It is a type of neuropathic pain. Phantom limb pain is a common experience of amputees. Local anesthetic injections into the nerves or sensitive areas of the stump may relieve pain for days, weeks or, sometimes permanently, despite the drug wearing off in a matter of hours; and small injections of hypertonic saline into the soft tissue between vertebrae produces local pain that radiates into the phantom limb for ten minutes or so and may be followed by hours, weeks or even longer of partial or total relief from phantom pain. Vigorous vibration or electrical stimulation of the stump, or current from electrodes surgically implanted onto the spinal cord all produce relief in some patients. Paraplegia, the loss of sensation and voluntary motor control after serious spinal cord damage, may be accompanied by girdle pain at the level of the spinal cord damage, visceral pain evoked by a filling bladder or bowel, or, in five to ten percent of paraplegics, phantom body pain in areas of complete sensory loss. This phantom body pain is initially described as burning or tingling but may evolve into severe crushing or pinching pain, fire running down the legs, or a knife twisting in the flesh. Onset may be immediate or may not occur until years after the disabling injury. Surgical treatment rarely provides lasting relief.

Psychogenic.

Psychogenic pain, also called psychalgia or somatoform pain, is pain caused, increased, or prolonged by mental, emotional, or behavioral factors. Headache, back pain, and stomach pain are sometimes diagnosed as psychogenic. Sufferers are often stigmatized, because both medical professionals and the general public tend to think that pain from a psychological source is not "real." However, specialists consider that it is no less actual or hurtful than pain from any other source. People with long term pain frequently display psychological disturbance, with elevated scores on the Minnesota Multiphasic Personality Inventory scales of hysteria, depression and hypochondriasis (the "neurotic triad"). Some investigators have argued that it is this neuroticism that causes acute injuries to turn chronic, but clinical evidence points the other way, to chronic pain causing neuroticism. When long term pain is relieved by therapeutic intervention, scores on the neurotic triad and anxiety fall, often to normal levels. Self-esteem, often low in chronic pain patients, also shows improvement once pain has resolved.

Breakthrough Pain.

Breakthrough pain is pain that comes on suddenly for short periods of time and is not alleviated by the patients' normal pain management. It is common in cancer patients who often have a background level of pain controlled by medications, but whose pain periodically "breaks through" the medication. The characteristics of breakthrough cancer pain vary from person to person and according to the cause.

Incident pain. Incident pain is pain that arises as a result of activity, such as movement of an arthritic joint, stretching a wound, etc.

A. Nociceptive Inflammatory Pain

Inflammatory pain is precipitated by an insult to the integrity of tissues at a cellular level. This can happen with penetration wounds, burns, extreme cold, fractures, arthritis, autoimmune conditions, excessive stretching, infections and vasoconstriction. During inflammation, a complex neuro-immune interaction results in primary hyperalgesia. A large range of inflammatory molecules induce and maintain the altered nociceptor sensitivity observed as hyperalgesia. This has been called the inflammatory "soup." These include compounds released or synthesised as a result of cellular breakdown, such as prostaglandins and bradykinin. The hyperaemia associated with inflammation delivers further mediators of hyperalgesia such as nitric oxide and bradykinin precursors. The primary afferent neuron itself secretes neuropeptides which can cause sensitisation Immune cells secrete a range of both pro- (e.g., cytokines, neurotrophins, serotonin and histamine) and anti-hyperalgesic molecules (e.g., opioids and cannabinoids).

This chemical soup of inflammatory mediators can directly affect nociceptors or may sensitize them to touch or movement, even at some distance from the inflammatory field. In this way one inflammatory mediator may sensitize more distant pain receptors to another inflammatory mediator. Inflammation-induced central sensitization, characterized by an enhanced neuronal activity in the spinal dorsal, is also an important component of inflammatory pain.

B. Neuropathic Pain

Neuropathic pain results from damage or disease affecting the somatosensory system. It may be associated with abnormal sensations called dysesthesia, and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Nociceptive pain, by contrast, is more commonly described as aching.

Up to 7% to 8% of the European population is affected and in 5% of persons it may be severe. Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain.

Central neuropathic pain is found in spinal cord injury, multiple sclerosis, and some strokes. Aside from diabetes (see diabetic neuropathy) and other metabolic conditions, the common causes of painful peripheral neuropathies are herpes zoster infection, HIV-related neuropathies, nutritional deficiencies, toxins, remote manifestations of malignancies, immune mediated disorders and physical trauma to a nerve trunk. Neuropathic pain is common in cancer as a direct result of cancer on peripheral nerves (e.g., compression by a tumor), or as a side effect of chemotherapy, radiation injury or surgery. The following are categories of neuropathic pain:

Peripheral. After a peripheral nerve lesion, aberrant regeneration may occur. Neurons become unusually sensitive and develop spontaneous pathological activity, abnormal excitability, and heightened sensitivity to chemical, thermal and mechanical stimuli. This phenomenon is called "peripheral sensitization."

Central. The (spinal cord) dorsal horn neurons give rise to the spinothalamic tract (STT), which constitutes the major ascending nociceptive pathway. As a consequence of ongoing spontaneous activity arising in the periphery, STT neurons develop increased background activity, enlarged receptive fields and increased responses to afferent impulses, including normally innocuous tactile stimuli. This phenomenon is called central sensitization. Central sensitization is an important mechanism of persistent neuropathic pain. Other mechanisms, however, may take place at the central level after peripheral nerve damage. The loss of afferent signals induces functional changes in dorsal horn neurons. A decrease in the large fiber input decreases activity of interneurons inhibiting nociceptive neurons, i.e., loss of afferent inhibition. Hypoactivity of the descending antinociceptive systems or loss of descending inhibition may be another factor. With loss of neuronal input (deafferentation) the STT neurons begin to fire spontaneously, a phenomenon designated "deafferentation hypersensitivity." Neuroglia ("glial cells") may play a role in central sensitization. Peripheral nerve injury induces glia to release proinflammatory cytokines and glutamate which, in turn influence neurons.

Mechanisms at light-microscopic and submicroscopic levels. The phenomena described above are dependent on changes at light-microscopic and submicroscopic levels. Altered expression of ion channels, changes in neurotransmitters and their receptors as well as altered gene expression in response to neural input are at play.

C. Current Therapies

The following is a discussion of different therapies currently applied against different types of pain conditions. Such is exemplary and not limiting.

1. Inflammatory Pain

Currently, there are a wide number of agents effective at treating nociceptive/inflammatory pain. These include salicylates, such as Aspirin (acetylsalicylic acid), Diflunisal and Salsalate, Propionic acid derivatives (Ibuprofen, Dexibuprofen, Naproxen, Fenoprofen, Ketoprofen, Dexketoprofen, Flurbiprofen, Oxaprozin, Loxoprofen), Acetic acid derivatives, (Indomethacin, Tolmetin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives or "Fenamates" (Mefenamic acid, Meclofenamic acid, Flufenamic acid, Tolfenamic acid), Selective COX-2 inhibitors (Celecoxib, Rofecoxib, Valdecoxib, Parecoxib, Lumiracoxib, Etoricoxib, Firocoxib), Sulphonanilides such as Nimesulide, and a range of other compounds (Licofelone, Lysine clonixinate, Hyperforin, Figwort).

2. Neuropathic Pain

Neuropathic pain can be very difficult to treat with only 40-60% of patients achieving partial relief, and determining the best treatment for individual patients remains challenging. Attempts to translate scientific studies into best practices are limited by factors such as differences in reference populations and a lack of head-to-head studies. Furthermore, multi-drug combinations and the needs of special populations, such as children, require more study.

It is common practice in medicine to designate classes of medication according to their most common or familiar use, e.g., as "antidepressants" and "anti-epileptic drugs" (AED's). These drugs have alternate uses to treat pain because the human nervous system employs common mechanisms for different functions, for example ion channels for impulse generation and neurotransmitters for cell-to-cell signaling. Favored treatments are certain antidepressants, e.g., tricyclics and selective serotonin-norepinephrine reuptake inhibitors (SNRI's), anticonvulsants, especially pregabalin (Lyrica) and gabapentin (Neurontin), and topical lidocaine. Opioid analgesics and tramadol are recognized as useful agents but are not recommended as first line treatments. Many of the pharmacologic treatments for chronic neuropathic pain decrease the sensitivity of nociceptive receptors, or desensitize C fibers such that they transmit fewer signals. Some drugs may exert their influence through descending pain modulating pathways. These descending pain modulating pathways originate in the brainstem.

Antidepressants.

The functioning of antidepressants is different in neuropathic pain from that observed in depression. Activation of descending norepinephrinergic and serotonergic pathways to the spinal cord limit pain signals ascending to the brain. Antidepressants will relieve neuropathic pain in non-depressed persons.

In animal models of neuropathic pain it has been found that compounds which only block serotonin reuptake do not improve neuropathic pain. Similarly, compounds that only block norepinephrine reuptake also do not improve neuropathic pain. Dual serotonin-norepinephrine reuptake inhibitors such as duloxetine, venlafaxine, and milnacipran, as well as tricyclic antidepressants such as amitriptyline, nortriptyline, and desipramine improve neuropathic pain and are considered first-line medications for this condition. Bupropion has been found to have efficacy in the treatment of neuropathic pain. Tricyclic antidepressants may also have effects on sodium channels.

Anticonvulsants.

Pregabalin (Lyrica) and gabapentin (Neurontin) work by blocking specific calcium channels on neurons and are preferred first-line medications for diabetic neuropathy. The anticonvulsants carbamazepine (Tegretol) and oxcarbazepine (Trileptal) are especially effective in trigeminal neuralgia. The actions of these two drugs are mediated principally through sodium channels.

Lamotrigine may have a special role in treating two conditions for which there are few alternatives, namely post stroke pain and HIV/AIDS-related neuropathy in patients already receiving antiretroviral therapy.

Opioids.

Opioids, also known as narcotics, are increasingly recognized as important treatment options for chronic pain. They are not considered first line treatments in neuropathic pain but remain the most consistently effective class of drugs for this condition. Opioids must be used only in appropriate individuals and under close medical supervision. Several opioids, particularly methadone, and ketobemidone possess NMDA antagonism in addition to their μ-opioid agonist properties. Methadone does so because it is a racemic mixture; only the l-isomer is a potent μ-opioid agonist. The d-isomer does not have opioid agonist action and acts as an NMDA antagonist; d-methadone is analgesic in experimental models of chronic pain. Clinical studies are in progress to test the efficacy of d-methadone in neuropathic pain syndromes.

Topical Agents.

In some forms of neuropathy, especially post-herpetic neuralgia, the topical application of local anesthetics such as lidocaine can provide relief. A transdermal patch containing lidocaine is available commercially in some countries. Repeated topical applications of capsaicin, are followed by a prolonged period of reduced skin sensibility referred to as desensitization, or nociceptor inactivation. Capsaicin not only depletes substance P but also results in a reversible degeneration of epidermal nerve fibers. Nevertheless, benefits appear to be modest with standard (low) strength preparations.

Cannabinoids.

Marijuana's active ingredients are called cannabinoids. Unfortunately, strongly held beliefs make discussion of the appropriate use of these substances, in a medical context, difficult. Similar considerations apply to opioids. A recent study showed smoked marijuana is beneficial in treating symptoms of HIV-associated peripheral neuropathy. Nabilone is an artificial cannabinoid which is significantly more potent than delta-9-tetrahydrocannabinol (THC). Nabilone produces less relief of chronic neuropathic pain and had slightly more side effects than dihydrocodeine. The predominant adverse effects are CNS depression and cardiovascular effects which are mild and well tolerated but, psychoactive side effects limit their use. A complicating issue may be a narrow therapeutic window; lower doses decrease pain but higher doses have the opposite effect.

Sativex, a fixed dose combination of delta-9-tetrahydrocannabinol (THC) and cannabidiol, is sold as an oromucosal spray. The product is approved in both Sweden[35] and Canada as adjunctive treatment for the symptomatic relief of neuropathic pain in multiple sclerosis, and for cancer related pain. Long-term studies are needed to assess the probability of weight gain, unwanted psychological influences and other adverse effects.

Botulinum Toxin Type A.

Botulinum toxin type A (BTX-A) is best known by its trade name, Botox. Local intradermal injection of BTX-A is helpful in chronic focal painful neuropathies. The analgesic effects are not dependent on changes in muscle tone. Benefits persist for at least 14 weeks from the time of administration. The utility of BTX-A in other painful conditions remains to be established.

NMDA Antagonism.

The N-methyl-D-aspartate (NMDA) receptor seems to play a major role in neuropathic pain and in the development of opioid tolerance. Dextromethorphan is an NMDA antagonist at high doses. Experiments in both animals and humans have established that NMDA antagonists such as ketamine and dextromethorphan can alleviate neuropathic pain and reverse opioid tolerance. Unfortunately, only a few NMDA antagonists are clinically available and their use is limited by a very short half life (dextromethorphan), weak activity (memantine) or unacceptable side effects (ketamine).

Reducing Sympathetic Nervous Stimulation.

In some neuropathic pain syndromes, "crosstalk" occurs between descending sympathetic nerves and ascending sensory nerves. Increases in sympathetic nervous system activity result in an increase of pain; this is known as sympathetically-mediated pain. Lesioning operations on the sympathetic branch of the autonomic nervous system are sometimes carried out. There are methods of treating sympathetically maintained pain in peripheral tissues. This is done topically to a patient having sympathetically maintained pain at a peripheral site where the pain originates. Wherein the sympathetically maintained pain can be diagnosed by local anesthetic blockade of the appropriate sympathetic ganglion or adrenergic receptor blockade via intravenous administration of phentolamine, and rekindled by intradermal injection of norepinephrine.

Dietary Supplements.

There are two dietary supplements that have clinical evidence showing them to be effective treatments of diabetic neuropathy; alpha lipoic acid and benfotiamine Administration of alpha lipoic acid (ALA) has been shown to reduce the various symptoms of peripheral diabetic neuropathy. While some studies on orally administered ALA had suggested a reduction in both the positive symptoms of diabetic neuropathy (including stabbing and burning pain) as well as neuropathic deficits (paresthesia), the metanalysis showed "more conflicting data whether it improves sensory symptoms or just neuropathic deficits alone." There is some limited evidence that ALA is also helpful in some other non-diabetic neuropathies.

Benfotiamine is a lipid-soluble form of thiamine that has several placebo-controlled double-blind trials proving efficacy in treating neuropathy and various other diabetic comorbidities.[46][47]

III. INHIBITORS

A. Peptides

1. Structure

The present invention, one embodiment, contemplates the design, production and use of various peptides that interfere with the interaction of USP5 with Cav3.2. The structural features of these peptides would normally be a portion of either molecule that is sufficient to bind to the cognate molecule and, in so doing, preventing binding of the full molecule from which the peptide is derived. An example is a peptide comprising the Cav3.2 linker III-IV domain, which effectively binds to USP5 and thus competes with natural Cav3.2 as the substrate. Many other peptides satisfying this role are possible. The peptides may have non-natural amino acid analog, and may include another peptide sequence (e.g., a tag sequence for purification, a stabilizing sequence, or a cell delivery domain).

In generally, the peptides have no more than 100 consecutive residues of a USP5 or Cav3.2 region, and may have no more than 75, 50, 40, 30, 25, or 20 residues. Thus, the term "a peptide having no more than X consecutive residues," even when including the term "comprising," cannot be understood to comprise a greater number of consecutive residues from the stated polypeptide. Second, the peptides will contain the motif that permits binding to a cognate molecule. Thus, the peptides will generally have, at a minimum, 20-75 consecutive residues of the native protein. In general, the peptides will be 75 residues or less, and comprising no more than about 50 consecutive residues. The overall length may be 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 residues. Ranges of peptide length of 10-75 residues, 15-75 residues, 20-75 residues, 30-75 residues, 10-65, residues, 15-65 residues, 20-65 residues, 30-65 residues, 10-50 residues, and 15-50 residues are contemplated. The number of consecutive residues may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 residues. Ranges of consecutive residues of 10-50 residues, 15-50 residues, 20-50 residues, 30-50 residues and 10-40 residues, 15-40, residues, 20-45 residues or 25-40 residues are contemplated.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally-occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length), while others are shown in Table 1, below.

TABLE 1

| CDD/CTD PEPTIDES | SEQ ID NO |
|---|---|
| QAATATRGRSAASRPTERPRAPARSASRPRRPVE | 3 |
| RQIKIWFQNRRMKWKK | 4 |
| RRMKWKK | 5 |
| RRWRRWWRRWWRRWRR | 6 |
| RGGRLSYSRRRFSTSTGR | 7 |
| YGRKKRRQRRR | 8 |
| RKKRRQRRR | 9 |
| YARAAARQARA | 10 |
| RRRRRRRR | 11 |
| KKKKKKKK | 12 |
| GWTLNSAGYLLGKINLKALAALAKXIL | 13 |
| LLILLRRRIRKQANAHSK | 14 |
| SRRHHCRSKAKRSRHH | 15 |
| NRARRNRRRVR | 16 |
| RQLRIAGRRLRGRSR | 17 |
| KLIKGRTPIKFGK | 18 |
| RRIPNRRPRR | 19 |

TABLE 1-continued

| CDD/CTD PEPTIDES | SEQ ID NO |
|---|---|
| KLALKLALKALKAALKLA | 20 |
| KLAKLAKKLAKLAK | 21 |
| GALFLGFLGAAGSTNGAWSQPKKKRKV | 22 |
| KETWWETWWTEWSQPKKKRKV | 23 |
| GALFLGWLGAAGSTMGAKKKRKV | 24 |
| MGLGLHLLVLAAALQGAKSKRKV | 25 |
| AAVALLPAVLLALLAPAAANYKKPKL | 26 |
| MANLGYWLLALFVTMWTDVGLCKKRPKP | 27 |
| LGTYTQDFNKFHTFPQTAIGVGAP | 28 |
| DPKGDPKGVTVTVTVTGKGDPXPD | 29 |
| PPPPPPPPPPPPPP | 30 |
| VRLPPPVRLPPPVRLPPP | 31 |
| PRPLPPPRPG | 32 |
| SVRRRPRPPYLPRPRPPPFFPPRLPPRIPP | 33 |
| TRSSRAGLQFPVGRVHRLLRK | 34 |
| GIGKFLHSAKKFGKAFVGEIMNS | 35 |
| KWKLFKKIEKVGQNIRDGIIKAGPAVAVVGQATQIAK | 36 |
| ALWMTLLKKVLKAAAKAALNAVLVGANA | 37 |
| GIGAVLKVLTTGLPALISWIKRKRQQ | 38 |
| INLKALAALAKKIL | 39 |
| GFFALIPKIISSPLPKTLLSAVGSALGGSGGQE | 40 |
| LAKWALKQGFAKLKS | 41 |
| SMAQDIISTIGDLVKWIIQTVNXFTKK | 42 |
| LLGDFFRKSKEKIGKEFKRIVQRIKQRIKDFLANLVPRTES | 43 |
| LKKLLKKLLKKLLKKLLKKL | 44 |
| KLKLKLKLKLKLKLKL | 45 |
| PAWRKAFRWAWRMLKKAA | 46 |

Peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

2. Synthesis

It will be advantageous to produce peptides using the solid-phase synthetic technique (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

3. Linkers

Linkers or cross-linking agents may be used to fuse peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge the physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., *Journal of the American Chemical Society*, 2000. 122(24): p. 5891-5892.

4. Design, Variants and Analogs

The present invention focuses on peptides comprising the USP5 and Cav3.2 sequences, but the inventors also contemplate that variants of these sequences may be employed. For example, certain non-natural amino acids that satisfy the structural constraints of the USP5 sequences may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155.

Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

B. Nucleic Acid Inhibitors

In certain embodiments, the USP5 inhibitor is a double-stranded RNA (dsRNA) directed to an mRNA for USP5. In such embodiments, the dsRNA mediates the reduction of the expression of USP5, which leads to reduced de-ubiquitination.

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). It is generally accepted that RNAi acts post-transcriptionally, targeting RNA transcripts for degradation. It appears that both nuclear and cytoplasmic RNA can be targeted (Bosher and Labouesse, 2000).

1. siRNA siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998). siRNA are well known in the art. For example, siRNA and double-stranded RNA have been described in U.S. Pat. Nos. 6,506,559 and 6,573,099, as well as in U.S. Patent Applications 2003/

0051263, 2003/0055020, 2004/0265839, 2002/0168707, 2003/0159161, and 2004/0064842, all of which are herein incorporated by reference in their entirety.

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

2. shRNA

Short hairpin RNA (shRNA) is a sequence of RNA that makes a tight hairpin turn that can be used to silence gene expression. shRNA is transcribed by RNA polymerase III. shRNA production in a mammalian cell can sometimes cause the cell to mount an interferon response as the cell seeks to defend itself from what it perceives as viral attack. Paddison et al. (2002) examined the importance of stem and loop length, sequence specificity, and presence of overhangs in determining shRNA activity. The authors found some interesting results. For example, they showed that the length of the stem and loop of functional shRNAs could vary. Stem lengths could range anywhere from 25 to 29 nt and loop size could range between 4 to 23 nt without affecting silencing activity. Presence of G-U mismatches between the 2 strands of the shRNA stem did not lead to a decrease in potency. Complementarity between the portion of the stem that binds to the target mRNA (antisense strand) and the mRNA, on the other hand, was shown to be critical. Single base mismatches between the antisense strand of the stem and the mRNA abolished silencing. It has been reported that presence of 2 nt 3'-overhangs is critical for siRNA activity (Elbashir et al., 2001). Presence of overhangs on shRNAs, however, did not seem to be important. Some of the functional shRNAs that were either chemically synthesized or in vitro transcribed, for example, did not have predicted 3' overhangs.

3. Production of Inhibitory Nucleic Acids dsRNA can be synthesized using well-described methods (Fire et al., 1998). Briefly, sense and antisense RNA are synthesized from DNA templates using T7 polymerase (MEGAscript, Ambion). After the synthesis is complete, the DNA template is digested with DNaseI and RNA purified by phenol/chloroform extraction and isopropanol precipitation. RNA size, purity and integrity are assayed on denaturing agarose gels. Sense and antisense RNA are diluted in potassium citrate buffer and annealed at 80° C. for 3 min to form dsRNA. As with the construction of DNA template libraries, a procedures may be used to aid this time intensive procedure. The sum of the individual dsRNA species is designated as a "dsRNA library."

The making of siRNAs has been mainly through direct chemical synthesis; through processing of longer, double-stranded RNAs through exposure to Drosophila embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25 mer lengths with the endogenous nuclease complex that converts long dsRNAs to siRNAs in vivo. They do not describe or present data for synthesizing and using in vitro transcribed 21-25 mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

Several groups have developed expression vectors that continually express siRNAs in stably transfected mammalian cells (Brummelkamp et al., 2002; Lee et al., 2002; Miyagishi and Taira, 2002; Paddison et al., 2002; Paul et al., 2002; Sui et al., 2002; Yu et al., 2002). Some of these plasmids are engineered to express shRNAs lacking poly (A) tails (Brummelkamp et al., 2002; Paddison et al., 2002; Paul et al., 2002; Yu et al., 2002) Transcription of shRNAs is initiated at a polymerase III (pol III) promoter and is believed to be terminated at position 2 of a 4-5-thymine transcription termination site, shRNAs are thought to fold into a stem-loop structure with 3' UU-overhangs. Subsequently, the ends of these shRNAs are processed, converting the shRNAs into ~21 nt siRNA-like molecules (Brummelkamp et al., 2002). The siRNA-like molecules can, in turn, bring about gene-specific silencing in the transfected mammalian cells.

More generally, most any oligo- or polynucleotide may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry an d solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

4. Nucleobases, Nucleosides, Nucleotides and Nucleic Analogs

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moeities comprise of from about 1, about 2, about 3, about 4, about 5, to about 6 carbon atoms. A nucleobase may be comprised in a nucleside or nucleotide, using any chemical or natural synthesis method described herein or known to one of ordinary skill in the art.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides, or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as flourescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moeity which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moeity replacing phosphodiester backbone moiety used for improved nuclease resistance, cellular uptake and regulating RNA expression; U.S. Pat. No. 5,858,988 which describes hydrophobic carrier agent attached to the 2'-O position of oligonuceotides to enhanced their membrane permeability and stability; U.S. Pat. No. 5,214,136 which describes olignucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate Rnase H; and U.S. Pat. No. 5,708,154 which describes RNA linked to a DNA to form a DNA-RNA hybrid.

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

A locked nucleic acid (LNA), often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. Such oligomers are commercially available. The locked ribose conformation enhances base stacking and backbone pre-organization. This significantly increases the thermal stability (melting temperature) of oligonucleotides (Kaur et al., 2006). LNA bases may be included in a DNA backbone, by they can also be in a backbone of LNA, 2'-O-methyl RNA, 2'-methoxyethyl RNA, or 2'-fluoro RNA. These molecules may utilize either a phosphodiester or phosphorothioate backbone.

Other oligonucleotide modifications can be made to produce oligomers of the present invention. For example, stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A motif having entirely of 2'-O-methyl and 2'-fluoro nucleotides has shown enhanced plasma stability and increased in vitro potency (Allerson et al., 2005). The incorporation of 2'-O-Me and 2'-O-MOE does not have a notable effect on activity (Prakash et al., 2005).

Sequences containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency.

In the boranophosphate linkage, a non-bridging phosphodiester oxygen is replaced by an isoelectronic borane (BH3-) moiety. Boranophosphate siRNAs (BNAs) have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

Certain terminal conjugates have been reported to improve or direct cellular uptake. For example, NAAs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of an oligonucleotides by means of a pyrrolidine linker does not result in a significant loss of gene-silencing activity in cell culture. These study demonstrates that cholesterol conjugation significantly improves in vivo pharmacological properties of oligonucleotides.

U.S. Patent Publication No. 2008/0015162, provide additional examples of nucleic acid analogs useful in the present invention. The following excerpts are derived from that document and are exemplary in nature only. In certain embodiments, oligomeric compounds comprise one or more modified monomers, including 2'-modified sugars, such as BNA's and monomers (e.g., nucleosides and nucleotides) with 2'-substituents such as allyl, amino, azido, thio, O-allyl, O—$C_1$-$C_{10}$ alkyl, —$OCF_3$, O—$(CH_2)_2$—O—$CH_3$, 2'-O $(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl.

In certain embodiments, the oligomeric compounds including, but no limited to short antisense compounds of the present invention, comprise one or more high affinity monomers provided that the oligomeric compound does not comprise a nucleotide comprising a 2'-O($CH_2$)$_n$H, wherein n is one to six. In certain embodiments, the oligomeric compounds including, but no limited to short antisense compounds of the present invention, comprise one or more high affinity monomer provided that the oligomeric compound does not comprise a nucleotide comprising a 2'-OCH$_3$ or a 2'-O(CH$_2$)$_2$OCH$_3$. In certain embodiments, the oligomeric compounds including, but no limited to short antisense compounds of the present invention, comprise one or more high affinity monomer provided that the oligomeric compound does not comprise a α-L-methyleneoxy (4'-CH$_2$—O-2') BNA. In certain embodiments, the oligomeric compounds comprise one or more high affinity monomer provided that the oligomeric compound does not comprise a β-D-methyleneoxy (4'-CH$_2$—O-2') BNA and/or a β-D-methyleneoxy (4'-CH$_2$—O-2') BNA.

Certain BNA's have been prepared and disclosed in the patent literature as well as in scientific literature (Singh et al., 1998; Koshkin et al., 1998; Wahlestedt et al., 2000; Kumar et al., 1998; WO 94/14226; WO 2005/021570; Singh et al., 1998). Examples of issued US patents and published applications that disclose BNA's include, for example, U.S. Pat. Nos. 7,053,207; 6,268,490; 6,770,748; 6,794,499; 7,034,133; and 6,525,191; and U.S. Patent Publication Nos. 2004/0171570; 2004/0219565; 2004/0014959; 2003/0207841; 2004/0143114; and 2003/0082807.

Also provided herein are BNAs in which the 2'-hydroxyl group of the ribosyl sugar ring is linked to the 4' carbon atom of the sugar ring thereby forming a methyleneoxy (4'-CH$_2$—O-2') linkage to form the bicyclic sugar moiety (reviewed in Elayadi et al., 2001; Braasch et al., 2001, and Orum et al., 2001; see also U.S. Pat. Nos. 6,268,490 and 6,670,461). The linkage can be a methylene (—CH$_2$—) group bridging the 2' oxygen atom and the 4' carbon atom, for which the term methyleneoxy (4'-CH$_2$—O-2') BNA is used for the bicyclic moiety; in the case of an ethylene group in this position, the term ethyleneoxy (4'-CH$_2$CH$_2$—O-2') BNA is used (Singh et al., 1998; Morita et al., 2002). Methyleneoxy (4'-CH$_2$—O-2') BNA and other bicyclic sugar analogs display very high duplex thermal stabilities with complementary DNA and RNA (T$_m$=+3 to +10° C.), stability towards 3'-exonucleolytic degradation and good solubility properties. Potent and nontoxic antisense oligonucleotides comprising BNAs have been described (Wahlestedt et al., 2000).

An isomer of methyleneoxy (4'-CH$_2$—O-2') BNA that has also been discussed is α-L-methyleneoxy (4'-CH$_2$—O-2') BNA which has been shown to have superior stability against a 3'-exonuclease. The α-L-methyleneoxy (4'-CH$_2$—O-2') BNA's were incorporated into antisense gapmers and chimeras that showed potent antisense activity (Frieden et al., 2003).

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., 1998). BNAs and preparation thereof are also described in WO 98/39352 and WO 99/14226.

Analogs of methyleneoxy (4'-CH$_2$—O-2') BNA, phosphorothioate-methyleneoxy (4'-CH$_2$—O-2') BNA and 2'-thio-BNAs, have also been prepared (Kumar et al., 1998). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., 1998). In addition, 2'-amino- and 2'-methylamino-BNA's have been prepared and the thermal stability of their duplexes with complementary RNA and DNA strands has been previously reported.

Modified sugar moieties are well known and can be used to alter, typically increase, the affinity of oligomers for its target and/or increase nuclease resistance. A representative list of modified sugars includes, but is not limited to, bicyclic modified sugars (BNA's), including methyleneoxy (4'-CH$_2$—O-2') BNA and ethyleneoxy (4'-(CH$_2$)$_2$—O-2' bridge) BNA; substituted sugars, especially 2'-substituted sugars having a 2'-F, 2'-OCH$_3$ or a 2'-O(CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

The naturally-occurring base portion of a nucleoside is typically a heterocyclic base. The two most common classes of such heterocyclic bases are the purines and the pyrimidines. For those nucleosides that include a pentofuranosyl sugar, a phosphate group can be linked to the 2', 3' or 5' hydroxyl moiety of the sugar. In forming oligonucleotides, those phosphate groups covalently link adjacent nucleosides to one another to form a linear polymeric compound. Within oligonucleotides, the phosphate groups are commonly referred to as forming the internucleotide backbone of the oligonucleotide. The naturally occurring linkage or backbone of RNA and of DNA is a 3' to 5' phosphodiester linkage.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

Described herein are linking groups that link monomers (including, but not limited to, modified and unmodified nucleosides and nucleotides) together, thereby forming an oligomeric compound. The two main classes of linking groups are defined by the presence or absence of a phosphorus atom. Representative phosphorus containing linkages include, but are not limited to, phosphodiesters (P=O), phosphotriesters, methylphosphonates, phosphoramidate, and phosphorothioates (P=S). Representative non-phosphorus containing linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Oligomeric compounds having non-phosphorus linking groups are referred to as oligonucleosides. Modified linkages, compared to natural phosphodiester linkages, can be used to alter, typically increase, nuclease resistance of the oligomeric compound. In certain embodiments, linkages having a chiral atom can be prepared a racemic mixtures, as separate enantiomers. Representative chiral linkages include, but are not limited to, alkylphosphonates and phosphorothioates. Methods of preparation of phosphorous-containing and non-phosphorous-containing linkages are well known to those skilled in the art.

5. Purification of Nucleic Acids

A nucleic acid may be purified on polyacrylamide gels, cesium chloride centrifugation gradients, or by any other means known to one of ordinary skill in the art (see for example, Sambrook et al., 2001, incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

IV. PHARMACEUTICAL FORMULATIONS AND ROUTES OF ADMINISTRATION

Where clinical applications in treating pain are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, intrathecal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Subjects

The methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

V. COMBINATION THERAPIES

Treating pain and avoiding tolerance to pain killers are major issues in clinical medicine. One goal of current research is to find ways to improve the efficacy of pain relief, as well as prevent the development of tolerance or addiction, and reduce side effects. One way is by combining such traditional therapies with the therapies of the present invention. In the context of the present invention, it is contemplated that an anti-USP5 therapy could be used similarly in conjunction with more standard pain intervention treatments.

The therapies would be provided in a combined amount effective to reduce pain in a subject, to reduce side effects associated with one or the other agent alone, or to avoid patient tolerance or addiction. This process may involve contacting the patient with the agents/therapies at the same time. This may be achieved by contacting the patient with a single composition or pharmacological formulation that includes both agents, or by contacting the cell with two distinct compositions or formulations, at the same time, wherein one composition includes the USP5 therapeutic and the other includes the agent.

Alternatively, the treatment according to the present invention may precede or follow the other treatment by intervals ranging from minutes to weeks. In embodiments where the standard treatment and the USP5 treatment are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the USP5 treatment or the other therapy will be desired. Various combinations may be employed, where the MUC1 peptide is "A," and the other therapy is "B," as exemplified below:

| | |
|---|---|
| A/B/A | B/B/A/A |
| B/A/B | B/A/B/A |
| B/B/A | B/A/A/B |
| A/A/B | B/B/B/A |
| B/A/A | A/A/A/B |
| A/B/B | B/A/A/A |
| B/B/B/A | A/B/A/A |
| B/B/A/B | A/A/B/A |
| A/A/B/B | A/B/B/B |
| A/B/A/B | B/A/B/B |
| A/B/B/A | B/B/A/B |

Other combinations are contemplated, including chronic dosing of one or both agents.

V. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Cell Culture and Transfection.

Human embryonic kidney tsA-201 cells were cultured as described previously (Altier et al., 2006). Cells were transfected with calcium phosphate and used for biochemical analysis 72 hrs post-transfection. Neuronal derived CAD cells were cultured as described previously (Altier et al., 2011). These cells were transfected with Lipofectamine 2000 (Invitrogen) and used for biochemical and electrophysiological experiments 48-72 hrs post-transfection. Both tsA-201 and CAD cells were preincubated with 5 µM MG132 (MG) or 100 µM Chloroquine (Chl) overnight.

Immunoprecipitation and Co-Immunoprecipitation Assays.

Cells were lysed in RIPA buffer (in mM; 50 Tris, 100 NaCl, 1% triton X-100, 1% NP-40, 0.2% SDS, 0.1% NaDeoxycholate, 20 NaF, 10 $Na_4P_2O_7$ pyrophosphate, 10 EDTA+ protease inhibitor cocktail, pH 7.5). A modified RIPA buffer (in mM; 50 Tris, 100 NaCl, 0.2% (v/v) triton X-100, 0.2% (v/v) NP-40, 10 EDTA+protease inhibitor cocktail, with or without 5 µM MG132 pH 7.5) was used to co-immunoprecipitate Cav3.2 channels with USP5 protein. Lysates from tsA-201, CAD cells and rat brain tissue were prepared by sonicating samples at 60% pulse for 10 seconds and by centrifugation at 13,000 rpm for 15 minutes at 4° C. Supernatants were transferred to new tubes and solubilized proteins were incubated with 50 µl of Protein G/A beads (Pierce) and 1 µg of HA antibody (Roche) or 2 µg of anti-Cav3.2 (H-300, Santa Cruz Biotechnologies, Inc., unless stated otherwise), anti-USP5 (ProteinTech Group, Inc.), anti-WWP1, anti-WWP2 (Sigma) and anti-USP15 (Abnova) antibodies overnight while tumbling at 4° C. Total inputs were taken from whole cell samples representing 4% of total protein and probed for actin. Immunoprecipitates were washed twice with (mM) 500 NaCl 50 Tris pH 7.5 buffer and once with 150 NaCl 50 Tris pH 7.5 buffer and co-immunoprecipitates were extensively washed with modified RIPA buffer, beads were aspirated to dryness. Laemmli buffer was added and samples were incubated at 96° C. for 7 minutes. Eluted samples were loaded on an 8% or 10% Tris-glycine gel and resolved using SDS-PAGE. Samples were transferred to 0.45 µm polyvinylidenedifluoride (PDVF) membranes (Millipore) and western blot analysis was performed using an anti-HA (Covance), anti-Cav3.2 (H-300, Santa Cruz Biotechnologies, Inc.), anti-ubiquitin (BD Pharmingen), anti-actin (Sigma), anti-USP15 (Abnova) and anti-USP5 (ProteinTech Group, Inc.) and anti-tubulin (Abcam) antibodies. Western blot quantification was performed using densitometry analysis (Quantity One-BioRad software). Student t-tests for unpaired data were performed to determine statistical significance. In each co-immunoprecipitation experiment, beads-only and IgG controls were performed—for space reasons, such controls were not always included in the figures.

Affinity Precipitation of Cav3.2-Interacting Proteins.

Total extracts from mouse DRG, dorsal horn and rat brain were prepared by centrifugation at 16,100 g for 30 minutes in buffer containing in mM; 50 Tris pH 7.6, 150 NaCl, 1% Triton X-100, 1% NP40, 10 EDTA, 10 EGTA and protease inhibitor cocktail (Roche). Lysates were sonicated at 60% pulse for 25 seconds and soluble proteins were collected by centrifugation at 16,100 g for 15 minutes at 4° C. Cav3.2-interacting proteins were collected by incubation with neutravidin-agarose beads (Thermo Scientific) while tumbling for 2 hrs at 4° C. with human $Cav3.2_{1556-1602}$, $Cav3.2_{1860-1884}$ or scrambled peptide for $Cav3.2_{1556-1602}$ covalently linked to a C-terminal biotin group (Genemed synthesis Inc. San Francisco, Calif.). Protein lysates were also incubated with neutravidin beads but no peptide as control. After extensive washing, bound proteins were analyzed by SDS-PAGE and visualized by Coomassie staining. Visible bands were excised and samples analyzed by MALDI/TOF-MS (Bruker Instruments Co., Bremen, Germany) and Nano-ESI-MS/MS on an API QSTAR-Pulsar (QSTAR, Applied Biosystems Div., Perkin-Elmer Corp., Foster City, Calif.).

Animals.

Male C57BL/6J (wild-type) or Cacna1h (Cav3.2 null) mice (22-28 g, 8 weeks old) were used. Animals were housed at a maximum of five per cage (30×20×15 cm) with ad libitum access to food and water. They were kept in controlled temperature of 23±1° C. on a 12 hr light/dark cycles (lights on at 7:00 a.m.). All testing procedures were performed following the protocol approved by the Institutional Animal Care and Use Committee and all efforts were made to minimize animal suffering according to the policies and recommendations of the International Association for the Study of Pain. Different cohorts of mice were used for each test, except when stated. The observer was blind to the experimental conditions in the experiment examining the effect of USP5-shRNA on acute pain (formalin test), the effect of Tat-peptides on chronic inflammatory pain (CFA model) in either wild-type or Cav3.2 null mice, the effects of Tat-peptides in long term CCI mice and in mibefradil treated animals. Cav3.2 null mice[1] were purchased from Jackson Labs.

Drugs and Reagents.

The following drugs were used in the study: Formaldehyde, Complete Freund's Adjuvant (CFA), mibefradil (Sigma Chemical Company, St. Louis, Mo., USA), human biotin-$Cav3.2_{1556-1602}$ biotin-$Cav3.2_{1569-1586}$, scrambled biotin-$Cav3.2_{1556-1602}$-III-IV linker, biotin-$Cav3.2_{1860-1884}$-CT, Tat-$Cav3.2_{1569-1589}$-III-IV, no-Tat $Cav3.2_{1569-1589}$ III IV, Tat-$Cav3.2$-$CT_{1860-1884}$, no-Tat-$Cav3.2$-$CT_{1860-1884}$ peptides (Genemed synthesis, Houston Tex.), USP5 and USP15shRNAs (Thermo Scientific, Open Biosystems). Recombinant long and short USP5 proteins where purchased from EnzoLifeSciences.

When drugs were delivered by the intraperitoneal (i.p.) route, a constant volume of 10 mL/kg body weight was injected. When drugs were administered intrathecally (i.t.), volumes of between 2-10 µl were injected in order to adjust the appropriate dose of solution injected. Appropriate vehicle-treated groups were assessed simultaneously.

Formalin Test.

The Formalin test is a widely used model that allows the evaluation of two different types of pain: neurogenic (first) and inflammatory (second) pain (Hunskaar & Hole, 1987; Dubuisson & Dennis, 1977). Animals received 20 µl of formalin solution (1.25%, made up in PBS) injected intraplantarly (i.pl.) in the ventral surface of the right hindpaw. Following intraplantar injection of formalin, animals were immediately placed individually in observation chambers and the time spent licking or biting the injected paw was recorded with a chronometer and considered as a nocifensive response. A blinded experimenter observed animals individually from 0-5 min (neurogenic phase) and 15-30 min (inflammatory phase). Mice received USP5-shRNA (12.5 µg/i.t.) or USP15-shRNA (control, 12.5 µg/i.t.) 1 day before they received formalin.

Chronic Constriction Injury (CCI)-Induced Neuropathy.

Neuropathic pain was induced by loose ligatures of sciatic nerve according to the method described by Bennett and Xie (1988) with minor modifications, and as performed previously in the inventors' laboratory (Gadotti & Zamponi, 2011). Mice were anaesthetized (isoflurane, 5% induction and 2.5% maintenance) and the right sciatic nerve was exposed at the level of the thigh by blunt dissection through the biceps femoris. Proximal to the sciatic nerve trifurcation, about 10 mm of nerve was freed of adhering tissue and 4 loose ligatures (silk suture 6-0) were loosely tied around it with about 1-2 mm spacing so that the epineural circulation was preserved. In sham-operated mice, the nerve was exposed but not injured. For the studies using USP5-shRNA treatment, same cohort of mice were analysed for either mechanical or thermal allodynia. Animals received USP5-shRNA (12.5 µg/i.t.) or USP15-shRNA (control, 12.5 µg/i.t.)

1 day before nerve injury in order to allow us to verify its prophylactic (pre-administered USP5-shRNA) effect. A second injection was given on the 12th day after nerve injury to determine the therapeutic action of the USP5-shRNA treatment. For experiments involving the Tat-peptides, mice received either Tat-3.2-III-IV (10.0 µg/i.t.) or Tat-3.2-CT (10.0 µg/i.t.) 5 days or 20 days after CCI.

CFA-Induced Persistent Inflammatory Pain.

In order to induce inflammatory chronic pain, mice received 20 µl of Complete Freund's Adjuvant (CFA) injected subcutaneously in the plantar surface of the right hindpaw (i.pl.) (Ferreira et al., 2001). Control groups received 20 µl of PBS in the ipsilateral paw. The dose of CFA produces significant hindpaw swelling and hypernociception that can be detected after 24 hour. Animals received USP5-shRNA (12.5 µg/i.t.) or USP15-shRNA (control, 12.5 µg/i.t.), or the Tat-peptides (10.0 µg/i.t. or 15.0 mg/kg, i.p.) 3 days following CFA injection.

Behavioral Assays.

Mechanical hyperalgesia was measured using the digital plantar aesthesiometer (DPA, UgoBasile, Varese, Italy). Animals were placed individually in a small enclosed testing arena (20 cm×18.5 cm×13 cm, length×width×height) on top of a wire mesh floor. Mice were allowed to acclimate for a period of at least 90 minutes. The DPA device was positioned beneath the animal, so that the filament was directly under the plantar surface of the ipsilateral hind paw. Each paw was tested three times per session. To evaluate the time-effect of the USP5-shRNA treatment, mechanical withdrawal thresholds were determined at 1 day prior to CFA injection (Baseline), and at 0, 3, 6, 9, 12, 24, 36, 48, 72 and 96 hours after CFA injection; or either at 1 day prior to CCI (Baseline), and at −1, 4, 7, 11, 14 and 18 days after CCI. For the Tat-peptide treatment, mechanical withdrawal was analyzed at 0, 15, 40, 90, 180 and 360 minutes after treatment, 5 days after CCI.

Thermal hyperalgesia was examined by measuring the latency to withdrawal of ipsilateral hind paws on a focused beam of radiant heat (IR=30) of a Plantar Test apparatus (UgoBasile, Varese, Italy). Animals were placed individually in a small enclosed testing arena (20 cm×18.5 cm×13 cm, length×width×height) on top of a wire mesh floor. Mice were allowed to acclimate for a period of at least 90 minutes. The device was positioned beneath the animal, so that the radiant heat was directly under the plantar surface of the ipsilateral hind paw. Three trials for each mouse were performed. The apparatus was set at a cut-off time of 20 s to avoid tissue damage. For USP5-shRNA treatment, thermal hyperalgesia was evaluated at −1, 3, 6, 10, 13 and 17 days after CCI.

Intrathecal Drug Treatment.

Injections were given to fully conscious mice using the method described by Hylden and Wilcox (Hylden & Wilcox, 1980). Animals were manually restrained, the dorsal fur of each mouse was shaved, the spinal column was arched, and a 30-gauge needle attached in a PE20 Polyethylene tube to a 25-µl Hamilton microsyringe (Hamilton, Birmingham, UK) was inserted into the subdural space between the $L_4$ and $L_5$ vertebrae. Correct i.t. positioning of the needle tip was confirmed by a characteristic tail-flick response of animal. Intrathecal injections of volumes between 2-10 µl were given over a period between 5-10 seconds. For intrathecal delivery of shRNA, no transfection reagents were added as these constructs are taken up into DRG neurons spontaneously. When mice were injected with the Tat III-IV linker peptide (10.0 µg/i.t.) in a concentration of 5 µg/µl over a period of 5 seconds, the inventors observed that 3 out of 10 mice developed shaking behavior which terminated no later than 15 minutes after injection. When mice received the same dose of the Tat III-IV linker peptide (10.0 µg/i.t.), but at a lower concentration (2.5 µg/µl) over a period of 10 seconds, no abnormal behavior was observed. In contrast, there were no noticeable behavioral consequences associated with intraperitoneal delivery of the TAT peptides. There was also no direct effect of the peptide on CFA induced inflammation per se (i.e., no changes in paw volume measured via a plethysmometer, paw diameter measured via a digital caliper, paw weight, and MPO).

Statistical Analysis.

For biochemical and electrophysiological analyses, data values are presented as mean±S.E.M. for n recorded cells. Statistical significance was determined using Student's t test: *$P<0.05$; $P<0.05$; *$P<0.05$; NS, statistically not different. For behavioral analyses, data are presented as means±SEM and evaluated by one-way, two-way or three-way analysis of variance (ANOVA) followed by Tukey's test. A value of $P<0.05$ was considered to be significant.

Cav3.2 T-Type Channel Antibodies.

The following antibodies against Cav3.2 channels were used: H-300 (Santa Cruz Biotechnologies) is directed against amino acids 2174-2353 in the C-terminus region and was used in the majority of the inventors' experiments, N-18 (Santa Cruz Biotechnologies) is directed against the N-terminus region, and 555-10 (Novus Biologicals) is an antibody against the domain II-III linker region. No cross reactivity of the H-300 antibody was observed on Western blots for tsA-201 cell lysate transfected with hCav3.1 and hCav3.3. Cav3.2 was also immunoprecipitated from WT and Cav3.2 null mouse tissue with the 555-10 antibody and western blots probed with H-300, revealing a specific (~250 kDa) band in WT, but not null mouse tissue.

Plasmids.

Cav3.2 linker from Cav3.2 full-length EGFP-C1 was subcloned into pBluescript II KS (+/−) using Sal 1 (~1.6 kb)-BamHI. pBluescript II-Cav3.2 III-IV linker single mutants K1560R, K1576R, K1587 and Y1594N (human sequence) were generated by PCR mutagenesis. Cav3.2 III-IV linker mutants were subcloned into Cav3.2 isoform 2-pcDNA3.1 using Sal1-BamHI. Wild type Cav3.2 isoform 2 cDNA was kindly provided by Dr. T. Snutch. Nedd4, WWP1 and WWP2 shRNA plasmids were purchased from Santa Cruz Biotechnology, Inc.

Heterologous Expression and Patch-Clamp Recordings in CAD Cells.

CAD cells were grown in a Dulbecco's modified Eagle's culture medium containing 10% fetal bovine serum and 1% penicillin/streptomycin and maintained under standard conditions at 37° C. in a humidified atmosphere containing 5% $CO_2$ and transiently transfected using phosphate-calcium buffer. CAD cells were transfected with shUSP5 along with EGFP in a ratio 1:0.1. In control experiments, shUSP5 was replaced by an equal amount of EGFP. Whole-cell $Ba^{2+}$ currents were recorded 48-72 hrs after transfection using pipettes (4-5 MΩ) filled with a solution containing (in mM): 110 CsCl, 3 Mg-ATP, 0.5 Na-GTP, 2.5 $MgCl_2$, 5 D-glucose, 10 EGTA, 10 HEPES (pH 7.3 with CsOH). The external solution contained (in mM): 10 $BaCl_2$, 1 $MgCl_2$, 140 TEACl, 10D-glucose, 10 HEPES (pH 7.2 with TEAOH). Whole-cell recording were performed using an Axopatch 200B amplifier (Axon Instruments, Union City, Calif.). Acquisition and analysis were performed using pClamp9 and Clampfit 9 software, respectively (Axon Instruments). All traces were corrected on-line for leak currents, digitized at 10 KHz and filtered at 2 KHz.

Harvesting of Dorsal Root Ganglia.

L4-6 dorsal root ganglia (DRGs) from 8 week old mice were dissected and collected in ice-cold dissection Hank's Buffered Salt Solution-HBSS (Invitrogen 14185-052) containing 0.25% 4-(2-hydroxyethyl)-1-piperazineethanesulfonic acid-HEPES (sigma H7523), osmolarity 310 mOsm and pH 7.2), then DRGs were washed once with fresh ice-cold dissection solution and cut into 2-3 pieces. DRG tissues were incubated at 37° C. in DMEM (Invitrogen 11995-073) containing 0.15% collagenase (Invitrogen 17018-029) for 90 minutes, followed by 0.25% trypsin-ethylenediaminetetraacetic acid (EDTA) (Invitrogen 25200-056) for another 10 min. DRG tissues were washed three times with warm complete culture medium (DMEM supplemented with 10% Heat inactivated fetal bovine serum (FBS) (Invitrogen 26140) and 1% penicillin/streptomycin (Invitrogen 15140)) to remove collagenase and trypsin enzymes. DRG neurons were dissociated by three to five passages through a fire-polished Pasteur pipette. Cells were plated on dishes pre-treated with poly-D-Lysine (Sigma P7280) and laminin (sigma L2020) and cells were kept at 37° C. in 5% $CO_2$ incubator. The next morning medium was replaced by fresh complete culture medium. Experiments were performed 12 hrs after cells were plated. Cells were preincubated with 5 μM MG132 (MG) or 100 μM Chloroquine (Chl) overnight. A set of experiments were done using ipsilateral lumbar 5 ($L_5$) mouse DRG harvested 90 minutes after treatment with Tat peptides and 3 days after CFA injection. For CCI experiments, dorsal horn was harvested 10 or 20 days after injury.

RNA Extraction, Reverse Transcription, and RT-PCR.

Total RNAs were prepared from pooled mouse lumbar sensory ganglia, lumbar spinal cord, brain, or from DRG primary culture using the TRIzol method according to the manufacturer's instructions (Invitrogen, Carlsbad, Calif.). RNAs were treated with DNase-I RNase-Free (Ambion, Austin, Tex.). Reverse transcriptions (RTs) were performed using total RNA with random primers and the Moloney murine leukemia virus reverse transcriptase (Invitrogen).

The expression levels of the long and short USP5 isoforms were estimated with a mix of common forward and reverse primers and a specific forward primer for the long form (Forward com 5' GTCAAGACCACGCGCTTT 3', Forward long specific 5' GCAACGAAGACGAAGACTCC 3', Reverse com 5' CAGCCCGCTCTAAGCTATTG 3'). This generated 2 bands for the long isoform (597 and 362 bp) and a single band for the short isoform (528 bp).

Immunohistofluorescence.

Mice (P-60 to P80) were anesthetized with pentobarbital injection and transcardially perfused with HBSS (pH 7.4, 4° C.). Lumbar spinal cords and lumbar DRGs were dissected from the perfused mice. Tissues were fixed in TBS containing 4% PFA (pH7.4) at room temperature for 30 and 60 minutes, respectively. Tissues were then washed three times 10 minutes in TBS at 4° C. and then embedded in 4% agarose and sectioned at 20-30 nm using a vibratome. Free floating section were blocked with TBS containing 0.05% tween 20 (TBST), 0.2% Triton X 100 and 10% normal goat serum at room temperature for 1 hr. Tissue sections were incubated with primary antibodies diluted in blocking solution at 4° C. overnight (rabbit anti-USP5 (Protein Tech 15158-1-AP, 1/500), mouse anti-NF200 (Sigma N0142, 1:200)). Then, sections were washed four times with TBST, and incubated with secondary antibodies (Alexa 568 conjugated goat anti rabbit, and Alexa 647 conjugated goat anti mouse antibodies (Invitrogen, 1/1000)), diluted in blocking solution at room temperature for 1 hr, washed again four times with TBST, and mounted on superfrost slides with Vectashield (Vectors laboratories). Alexa 488 conjugated IB4 (Invitrogen) was diluted at 1/200 and incubated together with secondary antibodies. For preabsorption experiments, recombinant USP5 protein (Sino Biological Inc, 12772-H08B) was incubated overnight at 4° C. with the anti-USP5 antibody at a 10/1 molar ratio. Following this step, classical immunohistofluorescence experiments performed as described with a direct comparison of labeling obtained with non preabsorbed and preabsorbed anti-USP5 antibodies. Confocal images were taken with a Zeiss LSM780 confocal microscope (at the Montpellier RIO imaging facility) and processed with Image J and photoshop CS4 software.

Example 2—Results

Cav3.2 Ubiquitination in Neurons from Mouse Dorsal Root Ganglia.

A key regulator of ion channel stability is their proteasomal degradation in response to ubiquitination. To determine if T-type channels are subject to ubiquitination, cultured mouse DRG neurons were harvested in the presence or the absence of the proteasome inhibitor MG132. Cav3.2 channels were immunoprecipitated and western blots were probed with a ubiquitin specific antibody. The inventors were able to detect a Cav3.2 ubiquitination signal only from immunoprecipitates from cells treated with 5 μM MG132 but not from cells treated with 100 μM chloroquine, a lysosomal inhibitor (FIG. 1A), indicating that Cav3.2 channels are ubiquitinated and degraded in the proteasome. Higher molecular weight bands consistent with channel aggregates were also evident in some of the Western blots probed with a Cav3.2 antibody (FIG. 1B, FIG. 8A), with these higher molecular weight bands appearing more abundant in MG132 treated cells. Ubiquitination of Cav3.2 channels was verified by mass spectrometry analysis of Cav3.2 channels expressed in tsA-201 cells (FIGS. 8A-B). A series of analogous experiments was performed in CAD cells, a neuron derived cell line that endogenously expresses Cav3.2 channels and that can easily be transfected (FIGS. 8C-F). Ubiquitination is also apparent in other members of the T-type channel family, Cav3.1 and Cav3.3 (FIGS. 9A-D).

To identify the ubiquitination site in Cav3.2, the inventors focused on the intracellular domain III-IV linker region of the channel as this region includes a number of lysine residues (i.e., the residues modified by ubiquitination) as well as a putative PY HECT E3 ubiquitin ligase binding motif (Staub et al., 1996) (FIG. 1C) that is conserved in all three Cav3.1, Cav3.2 and Cav3.3 channels. Indeed, HECT E3 ligases have been implicated in the regulation of cell surface density of ion channels and they play an important role in human diseases (Scheffner & Staub, 2007). To determine whether this region of the channel may be involved in ubiquitination, the inventors performed site directed mutagenesis of three individual lysine residues upstream from the PY motif (i.e., K1560R, K1576R and K1587R). They then carried out immunoprecipitations from transfected tsA-201 cells combined with western blot assays to analyze the ubiquitination level of these mutant channels. Ubiquitination of mutant Cav3.2 K1560R and Cav3.2 K1576R channels decreased by ~75% and ~25%, respectively, when compared to WT channels, whereas the K1587R mutant showed a similar ubiquitination signal as the WT channel (FIGS. 1D-F).

Altogether, these data strongly support the notion that Cav3.2 channels undergo ubiquitin modification, and that the intracellular III-IV loop is the target for E3 ubiquitin ligases and possibly for deubiquitinases.

Cav3.2 Surface Density is Regulated by WWP1 and WWP2.

To gain further insight into ubiquitin modification of Cav3.2 channels, the inventors used shRNAs directed against three different HECT E3 ligases WWP1, WWP2 and Nedd4. They first analyzed the ubiquitination levels of cell surface Cav3.2 channels from cells treated with shWWP1 (FIG. 10A) or with shWWP2. The inventors labeled tsA-201 cells (shRNA treated or untreated) with biotin, and the labelled surface pool of channels was enriched by immuno-precipitation using a Cav3.2 antibody and subsequently analyzed by western blot using a ubiquitin antibody. The surface pool of Cav3.2 channels from shWWP1 or shWWP2 transfected cells showed dramatically reduced ubiquitination signals (~23% and ~25% of control levels, respectively) (FIG. 2A). The inventors next examined the Cav3.2 surface and total protein levels under the same shRNA treatment conditions and the inventors confirmed an increase (~2 fold) in Cav3.2 cell surface expression levels when cells were depleted of WWP1 and WWP2 (FIGS. 2B-D), but not when cells were treated with Nedd4 shRNA (FIG. 2E), suggesting that WWP1 and WWP2 effectively regulate Cav3.2 cell surface density via ubiquitin modification.

Next, the inventors tested if WWP1 and WWP2 are able to bind to the III-IV linker region. The inventors created a 46 amino acid long III-IV linker peptide, hCav3.2$_{1556-1602}$, containing the PY motif or an 18 amino acid short peptide lacking the PY motif, hCav3.2$_{1569-1586}$ and these peptides were then incubated with mouse DRG lysates. The 46 amino acid long peptide encompassing almost the entire III-IV linker bound WWP1 (~104 kDa) (lane 1 in FIG. 2F). In contrast, binding of WWP2 (~98 kDa) could not be detected (FIG. 2G) suggesting that mouse DRG neurons, unlike tsA-201 cells, may not endogenously express this ligase. In the 18 amino acid peptide lacking the PY motif, WWP1 binding was reduced, albeit not completely eliminated (lane 2 in FIG. 2F), suggesting that the PY motif is not the sole determinant of WWP1 binding. This is confirmed by site directed mutagenesis experiments in which one of the two tyrosines of the PxYxxY motif was substituted with asparagine (FIGS. 10B-D). Analysis of such Cav3.2 Y1594N channels by immunoprecipitation and western blot showed a partial decrease in their ubiquitination level (~35%) (FIGS. 10B-D). Next, the inventors immunoprecipitated Cav3.2 channels from mouse DRG neurons and probed for either WWP1 or WWP2. As expected from the results in FIGS. 2F-G, only WWP1 co-immunoprecipitated with Cav3.2 channels in mouse DRG lysate (FIGS. 2H-I). A control experiment from whole mouse brain lysate indicates that WWP2 is in fact capable of interacting with Cav3.2 channels (FIG. 10E), in agreement with the inventors' shRNA data obtained in tsA-201 cells, and further supporting the idea that the inability to co-immunoprecipitate WWP2 with Cav3.2 channels from DRG lysate is due to lack of WWP2 expression in these cells.

Altogether, these data suggests that WWP1 and WWP2 can bind to Cav3.2 and regulate its ubiquitination state.

The Deubiquitinase USP5 Interacts with Cav3.2 Channels.

To determine if the domain III-IV linker interacts with other components of the ubiquitination machinery, the inventors took a proteomic approach. As bait, they selected the highly charged region in the domain III-IV linker (i.e., residues F1558-R1586), as this region contains the two lysines, K1560 and K1576 that are substrates for ubiquitin linkage (FIGS. 1D-G). Affinity precipitation assays using a biotinylated version of this peptide followed by mass spectrometry yielded several candidate interacting partners (FIG. 10F), including p97 (a protein involved in the proteasomal degradation pathway) and USP5 (or isopeptidase T), a deubiquitinase recently identified as part of the 26S proteasome (Besche et al., 2009). The inventors therefore hypothesized that Cav3.2 channel ubiquitination may be regulated by USP5. They first confirmed the inventors' mass-spectrometry result regarding the Cav3.2-USP5 interaction by means of affinity precipitation and co-immunoprecipitation assays. A biotinylated peptide (that corresponds to residues 1556-1602 of the III-IV linker of the human Cav3.2 isoform2) showed robust binding to USP5 from mouse brain lysate, whereas a scrambled Cav3.2$_{1556-1602}$ sequence or a Cav3.2 C-terminus peptide (CT corresponds to 1860-1884 human sequence) did not (FIG. 3A).

To determine if USP5 binds to the III-IV linker directly and not through a third partner present in the brain lysate, the inventors carried out in vitro binding assays with human USP5 recombinant proteins. As there is evidence of at least two USP5 splice isoforms present in human tissues (Falquet et al., 1995) (i.e., the long (858 amino acids, identifier: P45974-1, world-wide-web at uniprot.org/uniprot/P45974#P45974) and short (835 amino acids, identifier: P45974-2) forms), the inventors incubated both recombinant long and short hUSP5 proteins with hCav3.2$_{1556-1602}$ (III-IV linker) or hCav3.2$_{1860-1884}$ (CT) peptides. Both USP5 isoforms strongly bound to the Cav3.2 III-IV linker peptide but not to the Cav3.2 C-terminus peptide (FIGS. 3B-C) indicating that the effects of USP5 occur independently of USP5 splice variation.

To determine if there is an interaction between USP5 and Cav3.2 in mouse DRG neurons, the inventors carried out co-immunoprecipitation assays. Cav3.2 immunoprecipitates from mDRG neurons also show binding to USP5, seen as a ~97 kDa protein on SDS-PAGE (FIG. 3D). Experiments using brain lysate revealed that Cav3.3 channels weakly interact with USP5, whereas Cav3.1 do not (data not shown).

Overall these data demonstrate that USP5 binds to the III-IV linker of Cav3.2 in vitro and binds to the full-length channel in native tissue.

USP5 Affects Cav3.2 Ubiquitin Modification and Channel Activity.

To determine if USP5 is able to regulate Cav3.2 channel ubiquitination, the inventors transfected CAD cells (which express USP5 endogenously, FIG. 11A) with USP5 shRNA. Knockdown was verified and the level of Ca3.2 ubiquitination quantified by western blot analysis. As shown in FIGS. 11A-D, Cav3.2 immunoprecipitates from cells transfected with USP5-shRNA (and treated with 5 µM MG132) reveal a ~5-fold increase in channel ubiquitination when compared to immunoprecipitates from USP15-shRNA transfected cells (FIGS. 11B-D). As expected, Cav3.2 total protein levels were significantly reduced by USP5-shRNA treatment (FIG. 11C), likely due to ineffective deubiquitination and subsequent channel degradation. Altogether, these data indicate that USP5 is able to regulate ubiquitination levels of Cav3.2 in manner consistent with USP5 mediated deubiquitination.

To determine the functional consequences of USP5 knockdown, the inventors examined the effects of USP5-shRNA on whole cell T-type channel currents in CAD cells. As shown in FIG. 11E, Cav3.2 peak currents were decreased in CAD cells transfected with USP5-shRNA (+shUSP5: 1.4±0.2 pA/pF, n=18) when compared with peak currents obtained from control cells (GFP: 3.3±0.4 pA/pF, n=20), Students t-test: p<0.001) (FIG. 11E). Taken together these results indicate that ubiquitinated Cav3.2 channels are substrates for USP5 and that the association of the channel with USP5 results in altered whole cell Cav3.2 current densities.

Effect of USP5 Knockdown on Inflammatory Pain.

As noted earlier, Cav3.2 channels in DRG neurons play a major role in the transmission of nociceptive signaling and Cav3.2 channel activity is upregulated in models of inflammatory and neuropathic pain. The inventors thus wanted to determine if USP5 could modulate pain signaling via T-type channels. They initially tested the role of USP5 in both phases of the formalin model. The first phase of this model involves direct activation of nociceptive nerve terminals, whereas the second inflammatory pain phase is mediated by a combination of peripheral input and spinal cord sensitization (Hunskaar & Hole, 1987). Mice were treated via intrathecal (i.t.) injection of either USP5-shRNA or USP15-shRNA (both delivered at a dose of 12.5 µg/i.t. 1 day prior to pain testing) (FIG. 4A). A blind analysis demonstrated that upon USP5-shRNA treatment the nocifensive response time (i.e., time spent licking and biting the injected paw) was reduced, by 47±7% in the first phase (FIG. 4B) and 57±5% in the second phase (FIG. 4C). These data show that USP5-shRNA treatment modulates pain transmission and mediates analgesia when administered spinally to mice.

To determine whether USP5 modulates pain transmission under chronic inflammatory processes, the inventors analysed mechanical withdrawal threshold of USP5-shRNA treated animals after CFA injection. As shown in FIG. 4D, mice injected with CFA developed mechanical hyperalgesia as indicated by a significant decrease of paw withdrawal thresholds (P<0.001), when compared to pre-CFA baseline levels of the control group. Three days after CFA injection, treatment of mice with spinal USP5-shRNA (12.5 µg/i.t.) reversed mechanical hyperalgesia induced by CFA from 9 hours up to 3 days after treatment. In contrast, treatment of mice with spinal USP15-shRNA was ineffective (FIG. 4D). Collectively, these data indicate that USP5 is a regulator of chronic pain states accompanying inflammatory processes.

Effect of USP5 Knockdown on Neuropathic Pain.

To establish if USP5 also modulates pain signaling under neuropathic conditions, the inventors examined the prophylactic (1 day before injury,) and therapeutic (12 days after injury) action of USP5-shRNA in sciatic nerve injured (CCI)-mice. Sciatic nerve constriction triggered both mechanical (FIG. 4E) and thermal (FIG. 4F) hyperalgesia, as indicated by a significant decrease of mechanical and thermal withdrawal thresholds when compared to pre-CCI baseline levels of control group (P<0.01). Treatment of mice with spinal USP5-shRNA (12.5 µg/i.t., delivered 1 day before nerve injury) prevented the development of mechanical and thermal hyperalgesia as indicated by significant increases in mechanical and thermal withdrawal thresholds. This effect lasted for several days before returning to control levels at about day 10. Importantly, a second injection on day 12 re-established analgesia, indicating that USP5 knockdown can act both prophylactically, as well as therapeutically, although the second injection of USP5 shRNA appeared less effective than the prophylactic treatment. This may perhaps be due to the expression of other plastic (non T-type channel mediated) changes that could occur in response to development of pain. Altogether, these data indicate that USP5 is a major determinant of pain signaling in both inflammatory and neuropathic pain models.

Effect of a Tat-Cav3.2-III-IV Linker Peptide on Chronic Pain.

To determine if the effects of USP5 occurred via Cav3.2 T-type channels, the inventors designed Tat peptides with the intent of competitively disrupting USP5 binding to the Cav3.2 domain III-IV linker (FIG. 5A). The first verified that the Tat epitope would not interfere with USP5 binding to the Cav3.2$_{1569\text{-}1589}$ III-IV linker peptide by doing an in vitro affinity competition assay (FIG. 12A). The Tat-Cav3.2$_{1569\text{-}1589}$ III-IV linker peptide strongly bound to USP5 as shown by western blot and most importantly a non-biotinylated Tat-Cav3.2$_{1569\text{-}1589}$ III-IV linker peptide outcompeted the biotinylated Cav3.2$_{1569\text{-}1589}$ III-IV linker peptide for USP5, in contrast to the control non-biotinylated Tat-Cav3.2$_{1569\text{-}1589}$ C-terminus peptide (FIG. 12A). Next, the inventors performed a control experiment in transiently transfected tsA-201 cells to ensure that the Tat peptide did not directly block Cav3.2 channels (data not shown). The inventors then examined the effects of the III-IV linker Tat peptide (and as controls, a Tat-free III-IV linker peptide, and a Tat peptide directed against the C-terminus of the channel, see FIG. 5A) in inflammatory (CFA) and neuropathic (CCI) pain models. Once the reduced withdrawal thresholds to mechanical stimuli were firmly established in CFA-injected (P<0.001, 3 days after CFA) or CCI-injured mice (P<0.01, 5 days after surgery), animals received a single peptide injection either intrathecally (i.t., 10 µg/site) or intraperitoneally (i.p., 15 mg/kg, FIGS. 12A-C). Intrathecal delivery of the Tat-Cav3.2$_{1569\text{-}1589}$ III-IV linker peptide significantly (Two-way ANOVA) attenuated the mechanical hyperalgesia induced by CFA compared to animals injected with either the C-terminus peptide, or with III-IV linker peptides lacking the Tat epitope (FIG. 5B). Remarkably, the effect of the Tat III-IV linker peptide developed rapidly (over the time course of ~30 minutes) and persisted for up to six hours (FIG. 5B). Next, the inventors determined if the Tat peptide altered endogenous Cav3.2 protein levels in DRG neurons from CFA injected mice. Mice were treated with the Tat-3.2-III-IV linker or the Tat-3.2-CT peptides three days after they had received CFA, and 90 minutes later their ipsilateral lumbar ($L_5$) DRG were isolated and Cav3.2 levels analyzed by western blotting. The inventors found that total Cav3.2 levels were reduced by ~50% in mDRGs from CFA injected mice treated with the Tat-3.2-III-IV linker peptide compared with those treated with Tat-Cav3.2 CT peptide, or those from altogether naïve mice (FIGS. 5C-D). For technical reasons, the inventors could not specifically test cell surface protein expression of Cav3.2, however, the robust reduction in total Cav3.2 protein in Tat-3.2-III-IV linker treated DRGs is consistent with the analgesic effect of the peptide.

The Tat-3.2-III-IV linker peptide also produced significant and long-lasting (up to 6 hours) antihyperalgesia when delivered i.p. (15 mg/kg) compared to animals treated with the C-terminus control (FIG. 12B). No differences between Tat-3.2-III-IV linker and Tat-3.2-CT (control) peptides treated groups were found in naïve (non-injured) mice (FIG. 12C) indicating that the USP5 mediated regulation of T-type channels occurs only during chronic pain states and not under basal conditions.

The Tat-3.2-III-IV linker peptide delivered i.t. (10 µg/i.t.) also partially reversed the mechanical hyperalgesia in CCI-neuropathic mice (FIG. 5E). Paw withdrawal thresholds of animals treated with the Tat-3.2-III-IV linker peptide were significantly elevated when compared with the control Tat-3.2-CT peptide. As in the CFA model, the effects of the peptide fully developed in less than one hour, although the effects did not last as long in the CCI model. The inventors also tested whether the Tat-3.2-III-IV peptide retained its activity under longer term chronic pain conditions (i.e., three weeks after CCI). As shown in FIG. 5F, the Tat-3.2-III-IV peptide was able the reverse mechanical hyperalgesia 20 days after nerve injury.

To ensure that the effects of the Tat peptides were indeed specific for Cav3.2, the inventors carried out a series of experiments in Cav3.2 null mice. In response to CFA, these mice showed slightly higher mechanical withdrawal thresholds compared with WT animals, although this effect was not statistically significant (FIG. 6A). However, the Cav3.2 null mice were completely insensitive to the Tat-3.2-III-IV linker peptide (FIG. 6B). They also tested the effects of the Tat peptides in CFA treated mice in the presence of the T-type channel blocking compound mibefradil (i.t.). The inventors first assessed the dose and time dependence of the effects of mibefradil in CFA treated mice to optimize the experimental conditions (data not shown). They then delivered a maximally effective dose of mibefradil together with either the Tat-3.2-III-IV or the Tat-3.2-CT peptide as a control (FIG. 6C). While the Tat-3.2-III-IV peptide mediated a significant reversal of paw withdrawal thresholds in vehicle treated mice, it did not augment the effects of mibefradil. Altogether, these data strongly suggest that the USP5 mediates its effect on pain signaling specifically via its action on T-type calcium channels.

USP5 Regulates Cav3.2 Channels in Dorsal Horn Synapses.

It has been shown that T-type channels contribute to synaptic transmission in dorsal horn synapses, and that this contribution is enhanced under certain chronic pain conditions (Jacus et al., 2012). Because these nerve terminals originate from neurons whose cell bodies are localized in the DRG, it is possible that they may be an important locus of USP5 regulation of Cav3.2 channels. The inventors examined at the biochemical level the expression of USP5 in dorsal horn lysate in naïve and USP5 shRNA (i.t.) injected animals, revealing a robust reduction on USP5 expression in dorsal horn tissue (FIG. 7A). They were also able to co-immunoprecipitate USP5 and Cav3.2 channels from dorsal horn lysate (FIG. 7B), altogether showing that the USP5/Cav3.2 channel interaction persists in dorsal horn.

The inventors then asked whether chronic pain conditions might trigger an enhanced regulation of Cav3.2 channels by USP5. As shown in FIG. 7C-D, CFA injected animals display an enhanced expression of USP5 levels in the ipsilateral dorsal horn. Moreover, in chronically nerve injured mice, there is an enhanced association of Cav3.2 channels and USP5 as determined via co-immunoprecipitations (FIGS. 7E-F). Altogether, these data fit with a mechanism in which USP5 mediated regulation of Cav3.2 can occur physically and functionally in dorsal horn synapses, and is aberrantly enhanced in chronic pain conditions.

Example 3—Discussion

It is well established that aberrant T-type calcium channel activity occurs in chronic inflammatory and neuropathic pain states (Marger et al., 2011; Jagodic et al., 2007; Messinger et al., 200). Conversely, reducing T-type channel activity in primary afferent pain sensing neurons mediates analgesia, presumably by interfering with synaptic function in afferent nerve terminals and/or neuronal excitability (Jacus et al., 2012). Here, the inventors have presented novel evidence that ubiquitination and deubiquitination of Cav3.2 T-type channels is an important mechanism for regulation of T-type channel activity in primary pain sensing neurons. The data show that the Cav3.2 channel domain III-IV linker is a key regulatory site for channel stability. Furthermore, the inventors' data indicate that this site interacts with the E3 ubiquitin ligases of the WWP family, the deubiquitinase USP5, and that this region contains at least one lysine residue that is modified by ubiquitination. Hence, the domain III-IV linker of the channel is a hub for channel regulation that allows for control of channel activity/stability via ubiquitin modification (FIGS. 13A-B). In addition, although the inventors did not explore this here in detail, their proteomic screen identified p97 as another domain III-IV binding partner. This ATPase is known to regulate the interaction of substrates with the ubiquitination and deubiquitination machinery (Halawani and Latterich, 2006), further implicating the domain III-IV linker as a hotspot for channel regulation. These data show that WWP1 is able to ubiquitinate the channel, whereas USP5, but not a related deubiquitinase USP15, removes ubiquitin groups from the channel protein. This deubiquitination process then results in an increase in whole cell current density, which in the context of pain signaling, is expected to be pronociceptive for the reasons outlined above. Conversely, in vivo knockdown of USP5 with shRNA, or uncoupling USP5 from its binding site on the channel via delivery of Tat peptides mediated analgesic effects in both inflammatory and neuropathic pain models. In contrast, the Tat peptides did not affect basal pain behavior in naïve animals, indicating that under normal physiological conditions, Cav3.2 channels are either not regulated by USP5, or alternatively that T-type calcium channels do not contribute significantly to basal nociception.

It is likely that deubiquitinases such as USP5 have many cellular targets (Komander et al., 2009), which could in principle confound the interpretations of the in vivo studies, especially those involving USP5 knockdown. However, two lines of experiments support the idea that USP5 regulates pain via its modulation of T-type channels. First, uncoupling USP5 from Cav3.2 channels via Tat peptides directed to specific domain III-IV linker sequences mediated analgesia that was similar to that observed with USP5 knockdown. More importantly, these Tat peptides were completely ineffective in Cav3.2 knockout mice and in mice treated with mibefradil. Collectively, the inventors' data indicate that the pronociceptive effect of USP5 is due to its regulation of T-type channels rather than another cellular target.

It is interesting to note that Cav3.2 knockout mice showed a relatively normal withdrawal response to mechanical stimuli in the CFA model when compared to wild-type animals. This fits with findings of Wang and Lewin (2011) that demonstrated a reduced function of mechanoreceptors in Cav3.2 null mice with little effect on nociception. Along these lines, Choi et al. (2007) reported a normal sensitivity of Cav3.2 null mice to response to nerve injury. The inventors' observation that acute delivery of mibefradil was able to significantly attenuate pain in the CFA model (see FIG. 6C) on the other hand is consistent with a role of T-type channels in chronic pain conditions as reported by others (Bourinet et al., 2005; Jagodic et al., 2007; Messinger et al., 2009). The simplest explantion for this apparent discrepancy is the possible existence of compensatory mechanisms in the Cav3.2 null mice that maintain quasi normal nociceptive behavior, but which are insensitive to the USP5 interacting III-IV linker Tat peptide.

The stability of T-type channels is governed by a balance between ubiquitin ligase and deubiquitinase activity and the rate of degradation of ubiquitinated channels (FIGS. 13A-B). Alterations of either one of these processes during chronic pain could give rise to increased T-type channel protein levels in the plasma membrane. While very little is known about the WWP family of ligases and their regulation, there is a growing body of literature showing that deubiquitinases are under tight second messenger control and are activated by cellular pathways such as phosphatidylinositol 3-kinase (PI3K)/Akt which are upregulated during various pain states (Zhang et al., 2012; Yoshihara et al., 2012; Duan et al., 2012). The inventors' observation showing an enhanced expression of USP5 and an associated increase in its interaction with Cav3.2 channels in the ipsilateral dorsal horn of injured mice may hint at altered transcriptional regulation or trafficking of USP5 in the primary the afferent pain pathway and perhaps in spinal cord interneurons. Further experimentation will be needed to dissect the signaling steps that underlie this phenomenon. Nonetheless, the inventors' key finding is that T-type channel activity can be potently regulated by USP5, and that this regulation can be exploited to mediate analgesia in different forms of chronic pain. In principle, T-type channels could contribute to pain signalling in afferent fibers via multiple mechanisms, including the initiation of action potentials, a contribution to neuronal firing properties, and a participation in neurotransmitter release at dorsal horn synapse. Indeed, a recent study has revealed a contribution of T-type channels to glutamate release from synaptic terminals in dorsal horn lamina I and II, and that this effects is enhanced in a model of diabetic neuropathy (Jacus et al., 2012). A mechanism involving synaptic channels would be consistent with the rapid time course of action of intrathecally delivered interfering peptides, and with the observation that knockdown of USP5 via intrathecal delivery of shRNA reduced USP5 levels in dorsal horn tissue.

It is well established the ubiquitination and subsequent processing in the Endoplasmic Reticulum Associated protein Degradation (ERAD) complex is an important quality control mechanism that ensures expression of properly folded proteins. The ERAD system is a large protein complex that includes the ATPase p97 (which interacts with ubiquitinated proteins) catalyzes their retrotranslocation to the proteasomal degradation machinery (Romisch, 2005). This type of ubiquitination process is carried out by a large family of ER localized E3 ubiquitin ligases. For example, the inventors have recently shown that Cav1.2 L-type channels are ubiquitinated in the endoplasmic reticulum (ER) by the ubiquitin ligase RFP2 and then processed in the ERAD complex (Altier et al., 2011). In tsA-201 cells, >90% of the Cav3.2 channel pool is localized in intracellular compartments such as the ER (Souza and Zamponi, unpublished observations) where a similar quality control by the ERAD complex during forward trafficking could potentially take place. However, the functionally important pool of channels is the one that is present at the cell surface where a specific set of plasma membrane bound ubiquitin ligases are expressed. A notable example of an ion channel that is regulated in such a manner is the epithelial sodium channel, ENaC. This channel is ubiquitinated by the plasma membrane ubiquitin ligase Nedd4 (Staub et al., 1996; 1997; Abriel et al., 1999), internalized and then degraded via the proteasome pathway. These data show that Cav3.2 channels interact with the plasma membrane localized ubiquitin ligase WWP1 interacts with Cav3.2 channels in DRG neurons and that knockdown of WWP1 reduces ubiquitination and cell surface expression of these channels (see FIGS. 2A-I). This suggests that Cav3.2 channels are regulated by ubiquitination directly at the cell surface, in a manner that may be qualitatively similar to previous observations with ENaC. This may also explain the rapid time course of the physiological effects of intrathecally delivered III-IV linker Tat peptides, which would be more consistent with an effect on channel turnover in the plasma membrane, rather than modulation of ER export. This would not be without precedent, as USP2-45 has been shown to bind to and regulate the epithelial sodium channel, and USP10 has been reported to regulate the post-endocytic sorting of CFTR channels (Fakitsas et al., 2007; Oberfeld et al., 2011; Ruffieuex-Daidie et al., 2008; Bomberger et al., 2009). The observation that MG132 stabilized ubiquitinated Cav3.2 channels which suggests that Cav3.2 channel is ultimately targeted to the proteasome after internalization, perhaps similar to what has been described for ENaC. In this context it is interesting to note that certain types of chemotherapeutic drugs (such as bortezomib) are proteasome inhibitors whose side effects include the development of painful neuropathies (Meregalli et al., 2010), although it is not clear if this is mediated by an accumulation of T-type channels.

More than 90 different types of deubiquitinating enzymes have been identified in the human genome with varying subcellular distributions including nuclear, cytoplasmic and endocytic compartments (Nijman et al., 2005; Urbe, 2005). Their role in cell physiology has been widely recognized, and they are known to act on numerous cellular pathways to regulate protein stability and degradation. Deubiquitinases have been suggested as potential drug targets in a variety of disorders such as cancer, inflammation and neurological disorders (Daviet & Colland, 2008; Shanmugham & Ovaa, 2008; Hussain e al., 2009). Here, the inventors present evidence that deubiquitinases may also be important regulators of pain processing in the primary afferent pain pathway by virtue of increasing T-type channel stability. This in turn may open new therapeutic approaches for pain management through disrupting the USP5/channel interaction as the inventors have done here with the use of Tat peptides. The development of small organic drug molecules with a similar action would have the advantage of targeting a region that is unique in T-type calcium channels, thus potentially allowing for greater specificity compared with direct T-type channel blockers. Furthermore, disrupting the USP5/T-type channel interaction would specifically target a process that is involved in aberrant upregulation of channel activity, while presumably sparing normal channel function, thereby reducing the risk of adverse side effects.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference:
U.S. Pat. No. 5,440,013
U.S. Pat. No. 5,446,128

U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Patent Appln. 2005/0015232
Bodanszky et al., *J. Antibiot.*, 29(5):549-53, 1976.
Fischer, *Med. Res. Rev.*, 27(6):755-796, 2007.
Johnson et al., In: *Biotechnology And Pharmacy*, Pezzuto et al. (Eds.), Chapman and Hall, NY, 1993.
Merrifield, *J. Am. Chem. Soc.*, 85:2149-2154, 1963.
PCT Appln. PCT/US00/03745
PCT Appln. PCT/US00/14667
PCT Appln. PCT/US99/11913
PCT Appln. PCT/US99/18441
Peptide Synthesis, 1985
Protective Groups in Organic Chemistry, 1973
Protein NMR Spectroscopy, Principles and Practice, J. Cavanagh et al., Academic Press, San Diego, 1996.
Remington's Pharmaceutical Sciences, 15$^{th}$ Ed., 624-652, 1035-1038, 1570-1580, 1990.
Solid Phase Peptide Synthelia, 1984.
Catterall, W. A, & Few A. P. *Neuron* 59:882-901, 2008.
Andreasen et al., *Am J Physiol Renal Physiol* 279:F997-1005, 2000.
Bourinet, E., & Zamponi G. W., *Curr Top Med Chem* 5:539-546, 2005b.
Mangoni et al., *Prog Biophys Mol Biol*; 90:38-63, 2006.
McKay et al., *Eur JNeurosci* 24:2581-2594, 2006.
Molineux et al., *Proc Natl Acad Sci USA* 103:5555-5560, 2006.
Choi et al., *Genes Brain Behav* 6:425-431, 2007
Chen, C. C. et al., *Science* 302, 1416-8, 2003.
Perez-Reyes, E., *Physiol Rev* 83, 117-61, 2003.
Khosravani, H. & Zamponi, G. W., *Physiol Rev* 86, 941-66, 2006.
Bourinet et al., *Embo J* 24, 315-24, 2005a.
Zamponi et al., *Brain Res Rev* 60, 84-9, 2009.
Iftinca, M. C. & Zamponi, G. W., *Trends Pharmacol Sci* 30, 32-40, 2009.
Chemin et al., *J Physiol* 540, 3-14, 2002.
Weiss et al., *J Biol Chem* 287, 2810-8, 2012.
Jacus et al., *J Neurosci* 32, 9374-82, 2012.
Francois et al., *Pain* 154(2):283-93, 2013.
Marger et al., *Proc Natl Acad Sci USA* 108, 11268-73, 2011.
Jagodic et al., *J Neurosci* 27, 3305-16, 2007.
Messinger et al., *Pain* 145, 184-95, 2009.
Staub et al., *Embo J* 15, 2371-80, 1996.
Staub et al., *Embo J* 16, 6325-36, 1997.
Altier et al. *Nat Neurosci* 14, 173-80, 2011.
Younger et al., *J Cell Biol* 167, 1075-85, 2004.
Komander et al., *Nat Rev Mol Cell Biol* 10, 550-63, 2009.
Scheffner, M. & Staub, O., *BMC Biochem* 8 Suppl 1, S6, 2007.
Besche et al., *Biochemistry* 48, 2538-49, 2009.
Falquet et al., *FEBS Lett* 376, 233-7, 1995.
Talley et al., *JNeurosci* 19, 1895-911, 1999.
Shin et al., *Nat Neurosci* 6, 724-30, 2003.
Hunskaar, S. & Hole, K., *Pain* 30, 103-14, 1987.
Halawani, D. & Latterich, M., *Mol Cell* 22, 713-7, 2006.
Zhang et al., *Nat Cell Biol* 14, 717-26, 2012.
Yoshihara et al., *Biochem Biophys Res Commun* 423, 122-7, 2012.
Duan et al., *J Neurosci* 32, 6351-63, 2012.
Romisch, K., *Annu Rev Cell Dev Biol* 21, 435-56, 2005.
Abriel et cd., *J Clin Invest* 103, 667-73, 1999.
Fakitsas et al., *J Am Soc Nephrol* 18, 1084-92, 2007.
Oberfeld et al., *Am J Physiol Renal Physiol* 301, F189-96, 2011.
Ruffieux-Daidie et al., *J Am Soc Nephrol* 19, 2170-80, 2008.
Bomberger et al., *J Biol Chem* 284, 18778-89, 2009.
Meregalli et al., *Eur J Pain* 14, 343-50, 2010.
Nijman et al., *Cell* 123, 773-86, 2005.
Urbe, S., *Essays Biochem* 41, 81-98, 2005.
Daviet, L. & Colland, F., *Biochimie* 90, 270-83, 2008.
Shanmugham, A. & Ovaa, H., *Curr Opin Drug Discov Devel* 11, 688-96, 2008.
Hussain et al., *Cell Cycle* 8, 1688-97, 2009.
Allier et al., *Nat Neurosci* 9, 31-40, 2006.
Dubuisson, D. & Dennis, S. G., *Pain* 4, 161-74, 1977.
Bennett, G. J. & Xie, Y. K., *Pain* 33, 87-107, 1988.
Gadotti, V. M. & Zamponi, G. W., *Mol Pain* 7, 59, 2011.
Ferreira et al., *Neuropharmacology* 41, 1006-12, 2001.
Hylden, J. L. & Wilcox, G. L., *Eur J Pharmacol* 67, 313-6, 1980.
Wang & Lewin, *J. Physiol.* 589(9):2229-43, 2011.

---

The invention claimed is:

1. A method of inhibiting a Cav3.2 channel comprising contacting said channel in situ with an inhibitor of USP5 interaction with Cav3.2, wherein said inhibitor is a peptide that comprises SEQ ID NO: 1 but consists of no more than 75 residues Cav3.2, attached to a cell penetrating peptide domain.

2. The method of claim 1, wherein said cell penetrating peptide domain is a Tat domain.

3. A method of treating pain in a subject comprising administering to said subject a peptide that comprises SEQ ID NO: 1 but consisting of no more than 75 of Cav3.2, attached to a cell penetrating peptide domain.

4. The method of claim 3, wherein pain is inflammatory pain, neuropathic pain or chronic/persistent pain.

5. The method of claim 3, wherein said cell penetrating peptide domain is a Tat domain.

6. The method of claim 3, further comprising administering to said subject a second anti-pain agent.

7. The method of claim 3, wherein said inhibitor is administered systemically.

8. The method of claim 3, wherein said inhibitor is administered locally to an area of pain.

9. A pharmaceutical composition comprising a Cav3.2 peptide that comprises SEQ ID NO: 1 but consists of no more than 75 residues of Cav3.2, attached to a cell penetrating peptide domain.

10. The composition of claim 9, wherein said cell penetrating peptide domain is a Tat domain.

* * * * *

SEQUENCE LISTING

```
<160> NUMBER OF SEQ ID NOS: 46

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Glu Ala Arg Arg Arg Glu Glu Lys Arg Leu Arg Arg Leu Glu Arg Arg
1               5                   10                  15

Arg Arg Lys Ala Gln
            20
```

<210> SEQ ID NO 2
<211> LENGTH: 32
<212> TYPE: PRT
<213> ORGANISM: Artificial Sequence
<220> FEATURE:
<223> OTHER INFORMATION: Synthetic peptide

<400> SEQUENCE: 2

Tyr Gly Arg Lys Lys Arg Arg Gln Arg Arg Glu Ala Arg Arg
1               5                   10                  15

Glu Glu Lys Arg Leu Arg Arg Leu Glu Arg Arg Arg Lys Ala Gln
            20                  25                  30

<210> SEQ ID NO 3
<211> LENGTH: 34
<212> TYPE: PRT
<213> ORGANISM: Artificial Sequence
<220> FEATURE:
<223> OTHER INFORMATION: Synthetic peptide

<400> SEQUENCE: 3

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Arg Arg Met Lys Trp Lys Lys
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Arg Arg Trp Arg Arg Trp Trp Arg Arg Trp Trp Arg Arg Trp Arg Arg
1               5                   10                  15

<210> SEQ ID NO 7
<211> LENGTH: 18
<212> TYPE: PRT
<213> ORGANISM: Artificial Sequence
<220> FEATURE:

<223> OTHER INFORMATION: Synthetic peptide

<400> SEQUENCE: 7

Arg Gly Gly Arg Leu Ser Tyr Ser Arg Arg Arg Phe Ser Thr Ser Thr
1               5                   10                  15

Gly Arg

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Tyr Gly Arg Lys Lys Arg Arg Gln Arg Arg
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Arg Lys Lys Arg Arg Gln Arg Arg Arg
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

Tyr Ala Arg Ala Ala Ala Arg Gln Ala Arg Ala
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Arg Arg Arg Arg Arg Arg Arg Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Lys Lys Lys Lys Lys Lys Lys Lys
1               5

<210> SEQ ID NO 13
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 13

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide

<400> SEQUENCE: 14

Leu Leu Ile Leu Leu Arg Arg Arg Ile Arg Lys Gln Ala Asn Ala His
1               5                   10                  15

Ser Lys

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Ser Arg Arg His His Cys Arg Ser Lys Ala Lys Arg Ser Arg His His
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Asn Arg Ala Arg Arg Asn Arg Arg Arg Val Arg
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Arg Gln Leu Arg Ile Ala Gly Arg Arg Leu Arg Gly Arg Ser Arg
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

```
Lys Leu Ile Lys Gly Arg Thr Pro Ile Lys Phe Gly Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Arg Arg Ile Pro Asn Arg Arg Pro Arg Arg
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide

<400> SEQUENCE: 20

Lys Leu Ala Leu Lys Leu Ala Leu Lys Ala Leu Lys Ala Ala Leu Lys
1               5                   10                  15

Leu Ala

<210> SEQ ID NO 21
<211> LENGTH: 14
<212> TYPE: PRT
<213> ORGANISM: Artificial Sequence
<220> FEATURE:
<223> OTHER INFORMATION: Synthetic peptide

<400> SEQUENCE: 21

Lys Leu Ala Lys Leu Ala Lys Lys Leu Ala Lys Leu Ala Lys
1               5                   10

<210> SEQ ID NO 22
<211> LENGTH: 27
<212> TYPE: PRT
<213> ORGANISM: Artificial Sequence
<220> FEATURE:
<223> OTHER INFORMATION: Synthetic peptide

<400> SEQUENCE: 22

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 23
<211> LENGTH: 21
<212> TYPE: PRT
<213> ORGANISM: Artificial Sequence
<220> FEATURE:
<223> OTHER INFORMATION: Synthetic peptide

<400> SEQUENCE: 23

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 24
<211> LENGTH: 23
```

```
<212> TYPE: PRT
<213> ORGANISM: Artificial Sequence
<220> FEATURE:
<223> OTHER INFORMATION: Synthetic peptide

<400> SEQUENCE: 24

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 25
<211> LENGTH: 23
<212> TYPE: PRT
<213> ORGANISM: Artificial Sequence
<220> FEATURE:
<223> OTHER INFORMATION: Synthetic peptide

<400> SEQUENCE: 25

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 26
<211> LENGTH: 26
<212> TYPE: PRT
<213> ORGANISM: Artificial Sequence
<220> FEATURE:
<223> OTHER INFORMATION: Synthetic peptide

<400> SEQUENCE: 26

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 27
<211> LENGTH: 28
<212> TYPE: PRT
<213> ORGANISM: Artificial Sequence
<220> FEATURE:
<223> OTHER INFORMATION: Synthetic peptide

<400> SEQUENCE: 27

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 28
<211> LENGTH: 24
<212> TYPE: PRT
<213> ORGANISM: Artificial Sequence
<220> FEATURE:
<223> OTHER INFORMATION: Synthetic peptide

<400> SEQUENCE: 28

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 29
```

```
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 29

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 30
<211> LENGTH: 14
<212> TYPE: PRT
<213> ORGANISM: Artificial Sequence
<220> FEATURE:
<223> OTHER INFORMATION: Synthetic peptide

<400> SEQUENCE: 30

Pro Pro Pro Pro Pro Pro Pro Pro Pro Pro Pro Pro Pro Pro
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Synthetic peptide

<400> SEQUENCE: 31

Val Arg Leu Pro Pro Pro Val Arg Leu Pro Pro Pro Val Arg Leu Pro
1               5                   10                  15

Pro Pro

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32

Pro Arg Pro Leu Pro Pro Pro Arg Pro Gly
1               5                   10

<210> SEQ ID NO 33
<211> LENGTH: 30
<212> TYPE: PRT
<213> ORGANISM: Artificial Sequence
<220> FEATURE:
<223> OTHER INFORMATION: Synthetic peptide

<400> SEQUENCE: 33

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 34
<211> LENGTH: 21
<212> TYPE: PRT
```

```
<213> ORGANISM: Artificial Sequence
<220> FEATURE:
<223> OTHER INFORMATION: Synthetic peptide

<400> SEQUENCE: 34

Thr Arg Ser Ser Arg Ala Gly Leu Gln Phe Pro Val Gly Arg Val His
1               5                   10                  15

Arg Leu Leu Arg Lys
            20

<210> SEQ ID NO 35
<211> LENGTH: 23
<212> TYPE: PRT
<213> ORGANISM: Artificial Sequence
<220> FEATURE:
<223> OTHER INFORMATION: Synthetic peptide

<400> SEQUENCE: 35

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 36
<211> LENGTH: 37
<212> TYPE: PRT
<213> ORGANISM: Artificial Sequence
<220> FEATURE:
<223> OTHER INFORMATION: Synthetic peptide

<400> SEQUENCE: 36

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 37
<211> LENGTH: 28
<212> TYPE: PRT
<213> ORGANISM: Artificial Sequence
<220> FEATURE:
<223> OTHER INFORMATION: Synthetic peptide

<400> SEQUENCE: 37

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 38
<211> LENGTH: 26
<212> TYPE: PRT
<213> ORGANISM: Artificial Sequence
<220> FEATURE:
<223> OTHER INFORMATION: Synthetic peptide

<400> SEQUENCE: 38

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 39
<211> LENGTH: 14
<212> TYPE: PRT
<213> ORGANISM: Artificial Sequence
<220> FEATURE:
<223> OTHER INFORMATION: Synthetic peptide

<400> SEQUENCE: 39

Ile Asn Leu Lys Ala Leu Ala Ala Leu Ala Lys Lys Ile Leu
1               5                   10

<210> SEQ ID NO 40
<211> LENGTH: 33
<212> TYPE: PRT
<213> ORGANISM: Artificial Sequence
<220> FEATURE:
<223> OTHER INFORMATION: Synthetic peptide

<400> SEQUENCE: 40

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide

<400> SEQUENCE: 41

Leu Ala Lys Trp Ala Leu Lys Gln Gly Phe Ala Lys Leu Lys Ser
1               5                   10                  15

<210> SEQ ID NO 42
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 42

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 43
<211> LENGTH: 41
<212> TYPE: PRT
<213> ORGANISM: Artificial Sequence
<220> FEATURE:
<223> OTHER INFORMATION: Synthetic peptide

<400> SEQUENCE: 43

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
            20                  25                  30

```
Ala Asn Leu Val Pro Arg Thr Glu Ser
        35                  40

<210> SEQ ID NO 44
<211> LENGTH: 20
<212> TYPE: PRT
<213> ORGANISM: Artificial Sequence
<220> FEATURE:
<223> OTHER INFORMATION: Synthetic peptide

<400> SEQUENCE: 44

Leu Lys Lys Leu Leu Lys Lys Leu Leu Lys Lys Leu Leu Lys Lys Leu
1               5                   10                  15

Leu Lys Lys Leu
            20

<210> SEQ ID NO 45
<211> LENGTH: 18
<212> TYPE: PRT
<213> ORGANISM: Artificial Sequence
<220> FEATURE:
<223> OTHER INFORMATION: Synthetic peptide

<400> SEQUENCE: 45

Lys Leu Lys Leu Lys Leu Lys Leu Lys Leu Lys Leu Lys Leu Lys Leu
1               5                   10                  15

Lys Leu

<210> SEQ ID NO 46
<211> LENGTH: 18
<212> TYPE: PRT
<213> ORGANISM: Artificial Sequence
<220> FEATURE:
<223> OTHER INFORMATION: Synthetic peptide

<400> SEQUENCE: 46

Pro Ala Trp Arg Lys Ala Phe Arg Trp Ala Trp Arg Met Leu Lys Lys
1               5                   10                  15

Ala Ala
```